US011440887B2

(12) United States Patent
Kool et al.

(10) Patent No.: US 11,440,887 B2
(45) Date of Patent: Sep. 13, 2022

(54) SUBSTITUTED 1,2,3,4-TETRAHYDROQUINOLINES AS INHIBITORS OF REPAIR ENZYME 8-OXOGUANINE DEOXYRIBONUCLEIC ACID GLYCOSYLASE ACTIVITY

(71) Applicant: The Board of Trustees of the Leland Stanford Junior University, Stanford, CA (US)

(72) Inventors: Eric T. Kool, Stanford, CA (US); Yuki Tahara, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 163 days.

(21) Appl. No.: 16/637,594

(22) PCT Filed: Aug. 7, 2018

(86) PCT No.: PCT/US2018/045574
§ 371 (c)(1),
(2) Date: Feb. 7, 2020

(87) PCT Pub. No.: WO2019/032563
PCT Pub. Date: Feb. 14, 2019

(65) Prior Publication Data
US 2020/0190034 A1  Jun. 18, 2020

Related U.S. Application Data

(60) Provisional application No. 62/683,577, filed on Jun. 11, 2018, provisional application No. 62/542,157, filed on Aug. 7, 2017.

(51) Int. Cl.
*A61K 31/472* (2006.01)
*C07D 215/38* (2006.01)

(52) U.S. Cl.
CPC .................. *C07D 215/38* (2013.01)

(58) Field of Classification Search
CPC ........................ A61K 31/472; C07D 215/38
USPC ........................................ 514/311; 546/168
See application file for complete search history.

(56) References Cited

U.S. PATENT DOCUMENTS 6,300,342 B1  10/2001  Heckel et al.

FOREIGN PATENT DOCUMENTS

| EP | 3664790 A1 | 6/2020 |
| WO | 2009089042 A1 | 7/2009 |
| WO | 2017011834 A1 | 1/2017 |
| WO | 2017129069 A1 | 8/2017 |
| WO | 2019032563 A1 | 2/2019 |

OTHER PUBLICATIONS

International Preliminary Report on Patentability for International Application PCT/US2018/045574, Report dated Feb. 11, 2020, dated Feb. 20, 2020, 6 Pgs.
International Search Report and Written Opinion for International Application No. PCT/US2018/045574, Search completed Nov. 6, 2018, dated Dec. 3, 2018, 9 Pgs.
"Pubchem—CID: 7586257", Create Date: Jul. 29, 2006, pp. 1-13.
"Pubchem-CID: 18367204", Create Date: Dec. 4, 2007, pp. 1-14; pp. 4, Fig.
Aguilera-Aguirre et al., "Innate Inflammation Induced by the 8-Oxoguanine DNA Glycosylase-1-KRAS-NF-kB Pathway", The Journal of Immunology, vol. 193, No. 9, Nov. 1, 2014, pp. 4643-4653.
Ali et al., "OGG1 Mutations and Risk of Female Breast Cancer: Meta-Analysis and Experimental Data", Disease Markers, vol. 2015, No. 690878, May 19, 2015, pp. 1-16.
Anderson et al., "Role of Proto-oncogene Activation in Carcinogenesis", Environmental Health Perspectives, vol. 98, Nov. 1, 1992, pp. 13-24.
Bacsi et al., "Down-regulation of 8-oxoguanine DNA glycosylase 1 expression in the airway epithelium ameliorates allergic lung inflammation", DNA Repair, vol. 12, No. 1, Jan. 1, 2013, pp. 18-26.
Bauer et al., "The current state of eukaryotic DNA base damage and repair", Nucleic Acids Research, vol. 43, No. 21, Dec. 2, 2015, pp. 10083-10101.
Beharry et al., "Fluorescence Monitoring of the Oxidative Repair of DNA Alkylation Damage by ALKBH3, a Prostate Cancer Marker", Journal of the American Chemical Society, vol. 138, No. 11, Mar. 23, 2016, 11 pgs.
Carter et al., "Crystal Structure, biochemical and cellular activities demonstrate separate functions of MTH1 and MTH2", Nature Communications, vol. 6, No. 7871, Aug. 4, 2015, pp. 1-10.
Cedergren-Zeppezauer et al., "Crystal Structure of a dUTPase", Nature, vol. 355, Feb. 20, 1992, pp. 740-743.
Chatterjee et al., "Mechanisms of DNA Damage, Repair, and Mutagenesis", Environmental and Molecular Mutagenesis, vol. 58, No. 5, Jun. 2017, 29 pgs.

(Continued)

*Primary Examiner* — Douglas M Willis
(74) *Attorney, Agent, or Firm* — KPPB LLP

(57) ABSTRACT

Noncovalent small-molecule inhibitors of the enzyme OGG1, methods of their manufacture, and applications for their administration are provided. Small molecule inhibitors were shown to be selective for inhibiting OGG1 over multiple repair enzymes, including other base excision repair enzymes, and it displayed no toxicity in two human cell lines. The inhibitors provide a tool for the study of the role of OGG1 in multiple disease-related pathways, and a therapeutic target for the treatment thereof. Various embodiments include substituted 1,2,3,4-tetrahydroquinolines, such as compounds of the of the formula ABCDE:

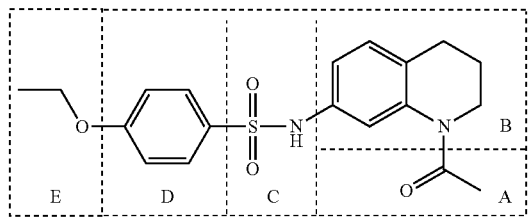

12 Claims, 30 Drawing Sheets

(56) References Cited

OTHER PUBLICATIONS

Das et al., "Association between OGG1 Ser326Cys polymorphism and risk of upper aero-digestive tract and gastrointestinal cancers: a meta-analysis", SpringerPlus, vol. 5, No. 227, Feb. 29, 2016, pp. 1-11.

De Bont et al., "Endogenous DNA damage in humans: a review of quantitative data", Mutagenesis, vol. 19, No. 3, May 2004, pp. 169-185.

Dietlein et al., "Cancer-specific defects in DNA repair pathways as targets for personalized therapeutic approaches", Cell Press, vol. 30, No. 8, Aug. 2014, pp. 326-339.

Dizdaroglu, "Free-radical-induced formation of an 8,5'-cyclo-2'-deoxyguanosine moiety in deoxyribonucleic acid", Biochemical Journal, vol. 238, No. 1, Aug. 1986, pp. 247-254.

Donley et al., "Small Molecule Inhibitors of 8-Oxoguanine DNA Glycosylase-1 (OGG1)", ACS Chemical Biology, vol. 10, No. 10, Oct. 16, 2015, pp. 2334-2343.

Edwards et al., "In Vitro Fluorogenic Real-Time Assay of the Repair of Oxidative DNA Damage", ChemBioChem, vol. 16, No. 11, Jul. 27, 2015, pp. 1637-1646.

Gavande et al., "DNA repair targeted therapy: The past or future of cancer treatment?", Pharmacology & Therapeutics, vol. 160, Apr. 2016, pp. 65-83.

Helleday et al., "DNA repair pathways as targets for cancer therapy", Nature Reviews Cancer, vol. 8, Mar. 2008, pp. 193-204.

Iyama et al., "NUDT16 is a (deoxy)inosine diphosphatase, and its deficiency induces accumulation of single-strand breaks in nuclear DNA and growth arrest", Nucleic Acids Research, vol. 38, No. 14, Apr. 12, 2010, pp. 4834-4843.

Ji et al., "A Chimeric ATP-Linked Nucleotide Enables Luminescence Signaling of Damage Surveillance by MTH1, a Cancer Target", Journal of the American Chemical Society, vol. 138, No. 29, Jul. 27, 2016, 11 pgs.

Kasai et al., "Formation of 8-hydroxyguanine moiety in cellular DNA by agents producing oxygen radicals and evidence for its repair", Carcinogenesis, vol. 7, No. 11, Nov. 1986, pp. 1849-1851.

Kasai et al., "Hydroxylation of deoxyguanosine at the C-8 position by ascorbic acid and other reducing agents", Nucleic Acids Research, vol. 12, No. 4, Feb. 24, 1984, pp. 2137-2145.

Kasai et al., "Hydroxylation of Guanine in Nucleosides and DNA at the C-8 Position by Heated Glucose and Oxygen Radical-Forming Agents", Environmental Health Perspectives, vol. 67, Aug. 1, 1986, pp. 111-116.

Kelley et al., "Targeting DNA repair pathways for cancer treatment: what's new?", Future Oncology, vol. 10, No. 7, Jun. 20, 2014, pp. 1215-1237.

Klungland et al., "Accumulation of premutagenic DNA lesions in mice defective in removal of oxidative base damage", PNAS, vol. 96, No. 23, Nov. 9, 1999, pp. 13300-13305.

Kozmin et al., "The formation of double-strand breaks at multiply damaged sites is driven by the kinetics of excision/incision at base damage in eukaryotic cells", Nucleic Acids Research, vol. 37, No. 6, Apr. 1, 2009, pp. 1767-1777.

Lipinski et al., "Experimental and computational approaches to estimate solubility and permeability in drug discovery and development settings", Advanced Drug Delivery Reviews, vol. 23, 1997, pp. 3-25.

Lu et al., "A mammalian DNA repair enzyme that excises oxidatively damaged guanines maps to a locus frequently lost in lung cancer", Current Biology, vol. 7, No. 6, Jun. 1, 1997, pp. 397-407.

Mahjabeen et al., "Deregulation of base excision repair gene expression and enhanced proliferation in head and neck squamous cell carcinoma", Tumor Biology, vol. 35, 2014, 13 pgs.

Mohan et al., "An Introduction to Inhibitors and Their Biological Applications", EMD Millipore, 2013, 27 pgs.

Nakabeppu, "Cellular Levels of 8-Oxoguanine in either DNA or the Nucleotide Pool Play Pivotal Roles in Carcinogenesis and Survival of Cancer Cells", International Journal of Molecular Sciences, vol. 15, No. 7, Jul. 15, 2014, pp. 12543-12557.

Ono et al., "Monitoring eukaryotic and bacterial UDG repair activity with DNA-multifluorophore sensors", Nucleic Acids Research, vol. 41, No. 12, Article e127, May 3, 2013, pp. 1-12.

Osterod et al., "Age-related and tissue-specific accumulation of oxidative DNA base damage in 7,8-dihydro-8-oxoguanine-DNA glycosylase (Ogg1) deficient mice", Carcinogenesis, vol. 22, No. 9, Sep. 2001, pp. 1459-1463.

Phillips et al., "Genotoxicity: damage to DNA and its consequences", Molecular, Clinical and Environmental Toxicology, Springer, Basel, vol. 1, 2009, pp. 87-110.

Rashad et al., "Facile Synthesis and Preliminary Structure—Activity Analysis of New Sulfonamides Against Trypanosoma brucei", ACS Medicinal Chemistry Letters, vol. 5, No. 5, May 8, 2014, pp. 496-500.

Singh et al., "Characterization of DNA with an 8-oxoguanine modification", Nucleic Acids Research, vol. 39, No. 15, Aug. 1, 2011, pp. 6789-6801.

Sugimura et al., "hOGG1 Ser326Cys Polymorphism and Lung Cancer Susceptibility", Cancer Epidemiology, Biomarkers & Prevention, vol. 8, No. 8, Aug. 1999, pp. 669-674.

Sundheim et al., "Human ABH3 structure and key residues for oxidative demethylation to reverse DNA/RNA damage", The EMBO Journal, vol. 25, No. 14, Jul. 26, 2006, pp. 3389-3397.

Yang et al., "Crystal structures of DNA/RNA repair enzymes AlkB and ABH2 bound to dsDNA", Nature, vol. 452, No. 7190, Apr. 24, 2008, 13 pgs.

Zhang et al., "Involvement of Nucleotide Excision and Mismatch Repair Mechanisms in Double Strand Break Repair", Current Genomics, vol. 10, No. 4, 2009, pp. 250-258.

Zhong et al., "The hOGG1Ser326Cys Polymorphism and Increased Lung Cancer Susceptibility in Caucasians: An Updated Meta-Analysis", Scientific Reports, vol. 2, No. 548, Jul. 31, 2012, pp. 1-7.

Abu-Shakra et al., "Formation of 8-hydroxy-2'-deoxyguanosine following treatment of 2'-deoxyguanosine or DNA by hydrogen peroxide or glutathione", Mutation Research/Genetic Toxicology and Environmental Mutagenesis, vol. 390, No. 1-2, Apr. 24, 1997, pp. 45-50.

Ames et al., "Endogenous mutagens and the causes of aging and cancer", Mutation Research/Fundamental and Molecular Mechanisms of Mutagenesis, vol. 250, No. 1-2, Sep.-Oct. 1991, pp. 3-16.

Cadet et al., "Oxidative damage to DNA: formation, measurement and biochemical features", Mutation Research/Fundamental and Molecular Mechanisms of Mutagenesis, vol. 531, No. 1-2, Oct. 29, 2003, pp. 5-23.

Chen et al., "Association of the C-285T and A5954G polymorphisms in the DNA repair gene OGG1 with the susceptibility of rheumatoid arthritis", Rheumatology International, vol. 32, 2012, pp. 1165-1169.

Chowdhury et al., "Tandem Mass Spectrometry-Based Detection of C4'-Oxidized Abasic Sites at Specific Positions in DNA Fragments", Chemical Research in Toxicology, vol. 22, No. 7, Jun. 4, 2009, pp. 1310-1319.

Cox et al., "Abbott Physicochemical Tiering (APT)—A unified approach to HTS triage", Bioorganic & Medicinal Chemistry, vol. 20, No. 14, Jul. 15, 2012, pp. 4564-4573.

Kasai et al., "Oral administration of the renal carcinogen, potassium bromate, specifically produces 8-hydroxydeoxyguanosine in rat target organ DNA", Carcinogenesis, vol. 8, No. 12, Dec. 1987, pp. 1959-1961.

Katagiri et al., "Synthesis, Structure, and Thermal Stability of Silver(I) Coordination Polymers with Bis(pyridyl) Ligands Linked by an Aromatic Sulfonamide: One-Dimensional-Straight Chain, One-Dimensional-Columnar with Helical Components, and Two-Dimensional-Layer Network", Crystal Growth & Design, vol. 14, No. 1, Jan. 2, 2014, pp. 199-206.

Nakabeppu, "Regulation of intracellular localization of human MTH1, OGG1, and MYH proteins for repair of oxidative DNA damage", Progress in Nucleic Acid Research and Molecular Biology, vol. 68, 2001, pp. 75-94.

(56) References Cited

OTHER PUBLICATIONS

Shibutani et al., "Insertion of specific bases during DNA synthesis past the oxidation-damaged base 8-oxodG", Nature, vol. 349, Jan. 31, 1991, pp. 431-434.
Sugiyama et al., "Specific detection of C-4' hydroxylated abasic sites generated by bleomycin and neocarzinostatin in DNA", Journal of the American Chemical Society, vol. 112, No. 13, Jun. 1, 1990, pp. 5252-5257.
Yoshimoto et al., "Use of Abasic Site-Containing DNA Strands for Nucleobase Recognition in Water", Journal of the American Chemical Society, vol. 125, No. 30, Jul. 2003, pp. 8982-8983.
Zhang et al., "Structural Basis of Substrate Specificity in Geobacter metallireducens SMUG1", ACS Chemical Biology, vol. 11, No. 6, Jun. 17, 2016, pp. 1729-1736.
Extended Search Report for European Application No. 18845059.7, Search completed Mar. 26, 2021, dated Apr. 12, 2021, 7 Pgs.
Tahara et al., "Potent and Selective Inhibitors of 8-Oxoguanine DNA Glycosylase", Journal of the American Chemical Society, vol. 140, No. 6, Feb. 14, 2018, pp. 2105-2114, DOI: 10.1021/jacs.7b09316.

```
┌─────────────────────────────────────────────────────────┐  202'
│ HTS of 25,975 compounds in the PubChem library          │
│ at a single 20 μM concentration                         │
└─────────────────────────────────────────────────────────┘
                            ▼
        ┌──────────────────────────────────────────┐  204'
        │ 8-points validation assay for 341 compounds │
        └──────────────────────────────────────────┘
                            ▼
              ┌──────────────────────────┐  206'
              │ Several hit compounds    │
              └──────────────────────────┘
                            ▼
```

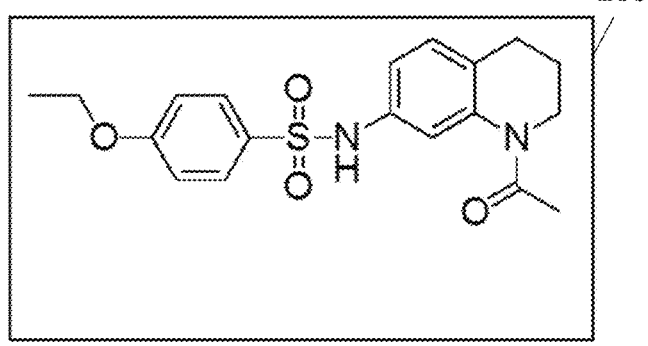

FIG. 2B

| 1 | SU0008 |  |
| 2 | SU0009 |  |
| 3 | SU0026 |  |
| 4 | SU0027 |  |
| 5 | SU0028 |  |
| 6 | SU0034 |  |
| 7 | SU0035 |  |

| # | ID | Structure |
|---|---|---|
| 8 | SU0036 | 4-ethoxyphenyl sulfonamide linked to 1-propanoyl-1,2,3,4-tetrahydroquinolin-7-yl |
| 9 | SU0037 | 4-ethoxyphenyl sulfonamide linked to 1-benzoyl-1,2,3,4-tetrahydroquinolin-7-yl |
| 10 | SU0044 | phenyl sulfonamide linked to 1-acetyl-1,2,3,4-tetrahydroquinolin-7-yl |
| 11 | SU0045 | 4-methylphenyl sulfonamide linked to 1-acetyl-1,2,3,4-tetrahydroquinolin-7-yl |
| 12 | SU0059 | 4-(trifluoromethoxy)phenyl sulfonamide linked to 1-propanoyl-1,2,3,4-tetrahydroquinolin-7-yl |
| 13 | SU0064 | 4-ethoxyphenyl sulfonamide linked to 1-(cyclopropanecarbonyl)-1,2,3,4-tetrahydroquinolin-7-yl |
| 14 | SU0065 | 4-ethoxyphenyl sulfonamide linked to 1-(phenylacetyl)-1,2,3,4-tetrahydroquinolin-7-yl |

FIG. 4B

| 15 | SU0066 | (structure: ethylsulfonamide-tetrahydroquinoline with N-propionyl) |
| 16 | SU0070 | (structure: 4-acetamidobenzenesulfonamide-tetrahydroquinoline with N-propionyl) |
| 17 | SU0071 | (structure: 4-acetylbenzenesulfonamide-tetrahydroquinoline with N-propionyl) |
| 18 | SU0075 | (structure: 4-ethoxybenzenesulfonamide-3-acetamidophenyl) |
| 19 | SU0077 | (structure: 4-ethoxybenzenesulfonamide-tetrahydroquinoline with N-isobutyryl) |
| 20 | SU0080 | (structure: 4-isopropoxybenzenesulfonamide-tetrahydroquinoline with N-propionyl) |
| 21 | SU0081 | (structure: 4-ethoxybenzenesulfonamide-tetrahydroquinoline with N-COCH$_2$CF$_3$) |

FIG. 4C

| 22 | SU0084 |  |
| 23 | SU0086 |  |
| 24 | SU0087 |  |
| 25 | SU0091 |  |
| 26 | SU0097 |  |
| 27 | SU0098 |  |
| 28 | SU0101 |  |

| 29 | SU0108 | |
| --- | --- | --- |
| 30 | SU0112 | |
| 31 | SU0113 | |
| 32 | SU0116 | |
| 33 | SU0117 | |
| 34 | SU0119 | |
| 35 | SU0120 | |

FIG. 4E

| | | |
|---|---|---|
| 36 | SU0121 |  |
| 37 | SU0123 |  |
| 38 | SU0130 |  |
| 39 | SU0132 |  |
| 40 | SU0133 |  |
| 41 | SU0134 |  |
| 42 | SU0135 |  |

| 43 | SU0136 | |
| 44 | SU0142 | |
| 45 | SU0143 | |
| 46 | SU0146 | |
| 47 | SU0156 | |
| 48 | SU0157 | |
| 49 | SU0159 | |

FIG. 4G

| 50 | SU0160 |  |
| 51 | SU0161 |  |
| 52 | SU0166 |  |
| 53 | SU0172 |  |
| 54 | SU0175 |  |
| 55 | SU0177 |  |
| 56 | SU0185 |  |

| 57 | SU0190 | |
| 58 | SU0192 | |
| 59 | SU0194 | |
| 60 | SU0204 | |
| 61 | SU0205 | |
| 62 | SU0206 | |
| 63 | SU0208 | |

FIG. 4I

| | | |
|---|---|---|
| 64 | SU0211 |  |
| 65 | SU0222 |  |
| 66 | SU0223 |  |
| 67 | SU0230 |  |
| 68 | SU0232 |  |
| 69 | SU0236 |  |
| 70 | SU0237 |  |

| 71 | SU0239 |  |
| 72 | SU0242 |  |
| 73 | SU0243 |  |
| 74 | SU0244 |  |
| 75 | SU0245 |  |
| 76 | SU0251 |  |
| 77 | SU0252 |  |

| # | ID | Structure |
|---|---|---|
| 78 | SU0254 | 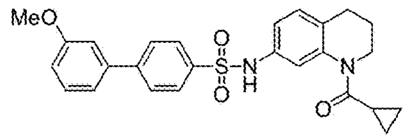 |
| 79 | SU0257 | 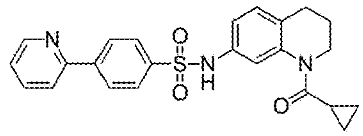 |
| 80 | SU0259 | 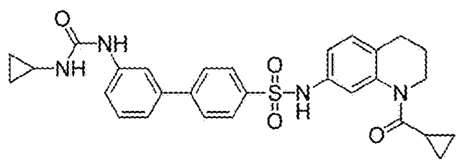 |
| 81 | SU0260 | 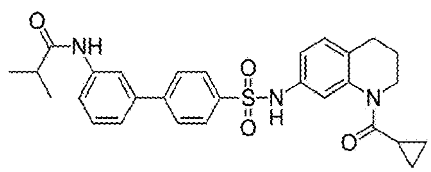 |
| 82 | SU0261 | 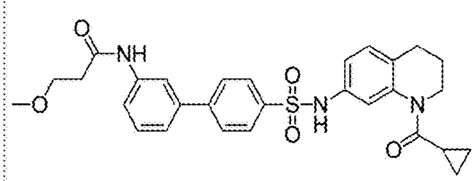 |
| 83 | SU0266 | 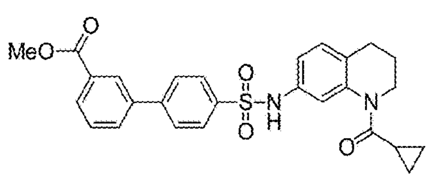 |
| 84 | SU0267 | 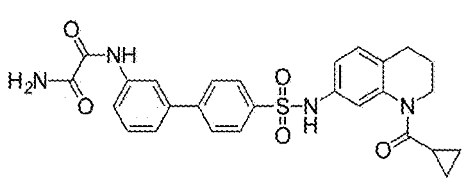 |

FIG. 4L

| 85 | SU0268 | ![structure] |
| 86 | SU0269 | ![structure] |
| 87 | SU0270 | ![structure] |

FIG. 4M

| Time (hr) | Oral (3 mg/kg) | | | | |
|---|---|---|---|---|---|
| | Mouse # | | | | |
| | 443 | 444 | 445 | Mean | SD |
| 0 (pre-dose) | BLOQ | BLOQ | BLOQ | ND | ND |
| 0.25 | 21.6 | 10.9 | 33.1 | 21.9 | 11.1 |
| 0.50 | 8.02 | 4.94 | 18.9 | 10.6 | 7.33 |
| 1.0 | 4.46 | 3.40 | 14.6 | 7.49 | 6.18 |
| 2.0 | 1.53 | 2.51 | 8.73 | 4.26 | 3.90 |
| 4.0 | BLOQ | 1.22 | 3.30 | 2.26 | ND |
| 8.0 | BLOQ | BLOQ | BLOQ | ND | ND |
| 24 | BLOQ | BLOQ | BLOQ | ND | ND |
| Animal Weight (kg) | 0.034 | 0.031 | 0.034 | 0.033 | 0.002 |
| Volume Dosed (mL) | 0.51 | 0.47 | 0.51 | 0.497 | 0.023 |
| $C_{max}$ (ng/mL) | 21.6 | 10.9 | 33.1 | 21.9 | 11.1 |
| $t_{max}$ (hr) | 0.25 | 0.25 | 0.25 | 0.25 | 0.00 |
| $t_{1/2}$ (hr) | 0.630 | 2.01 | 1.39 | 1.35 | 0.692 |
| $MRT_{last}$ (hr) | 0.617 | 1.37 | 1.31 | 1.10 | 0.418 |
| $AUC_{last}$ (hr·ng/mL) | 12.5 | 12.1 | 42.7 | 22.4 | 17.5 |
| $AUC_\infty$ (hr·ng/mL) | 13.9 | 15.7 | 49.3 | 26.3 | 20.0 |
| Dose-normalized Values[2] | | | | | |
| $AUC_{last}$ (hr·kg·ng/mL/mg) | 4.17 | 4.04 | 14.2 | 7.48 | 5.85 |
| $AUC_\infty$ (hr·kg·ng/mL/mg) | 4.64 | 5.22 | 16.4 | 8.77 | 6.66 |

$C_{max}$: maximum blood concentration; $t_{max}$: time of maximum blood concentration; $t_{1/2}$: half-life, data points used for half-life determination are in bold; $MRT_{last}$: mean residence time, calculated to the last observable time point; AUClast: area under the curve, calculated to the last observable time point; $AUC_\infty$: area under the curve, extrapolated to infinity; ND: not determined; BLOQ: below the limit of quantitation (1.0 ng/mL).
[2]Dose-normalized by dividing the parameter by the nominal dose in mg/kg.

FIG. 14A

| Intraperitoneal (3 mg/kg, SU0268) | | | | | |
|---|---|---|---|---|---|
| Time (hr) | Mouse # | | | Mean | SD |
| | 340 | 341 | 342 | | |
| 0 (pre-dose) | BLOQ | BLOQ | BLOQ | ND | ND |
| 0.083 | 412 | 372 | 203 | 329 | 111 |
| 0.25 | 999 | 1410 | 1220 | 1210 | 206 |
| 0.50 | 513 | 1530 | 713 | 919 | 539 |
| 1.0 | 205 | 813 | 419 | 479 | 308 |
| 2.0 | 35.6 | 220 | 97.2 | 118 | 93.9 |
| 4.0 | 55.8 | 168 | 86.4 | 103 | 58.0 |
| 8.0 | 11.2 | 19.5 | 8.30 | 13.0 | 5.81 |
| 24 | 1.95 | 2.97 | 1.36 | 2.09 | 0.815 |
| Animal Weight (kg) | 0.031 | 0.030 | 0.027 | 0.029 | 0.002 |
| Volume Dosed (mL) | 0.47 | 0.45 | 0.41 | 0.44 | 0.03 |
| $C_{max}$ (ng/mL) | 999 | 1530 | 1220 | 1250 | 267 |
| $t_{max}$ (hr) | 0.25 | 0.5 | 0.25 | 0.33 | 0.14 |
| $t_{1/2}$ (hr) | 4.84 | 3.62 | 3.60 | 4.02 | 0.709 |
| $MRT_{last}$ (hr) | 2.47 | 2.24 | 2.03 | 2.25 | 0.216 |
| $AUC_{last}$ (hr·ng/mL) | 954 | 2577 | 1360 | 1630 | 844 |
| $AUC_{\infty}$ (hr·ng/mL) | 968 | 2592 | 1367 | 1642 | 846 |
| Dose-normalized Values[1] | | | | | |
| $AUC_{last}$ (hr·kg·ng/mL/mg) | 318 | 859 | 453 | 543 | 281 |
| $AUC_{\infty}$ (hr·kg·ng/mL/mg) | 323 | 864 | 456 | 547 | 282 |

$C_{max}$: maximum blood concentration; $t_{max}$: time of maximum blood concentration; $t_{1/2}$: half-life, data points used for half-life determination are in bold; $MRT_{last}$: mean residence time, calculated to the last observable time point; AUClast: area under the curve, calculated to the last observable time point; $AUC_{\infty}$: area under the curve, extrapolated to infinity; ND: not determined; BLOQ: below the limit of quantitation (1.0 ng/mL).
[1] Dose-normalized by dividing the parameter by the nominal dose in mg/kg.

FIG. 14B

| Time (hr) | Intraperitoneal (3 mg/kg) | | | | |
|---|---|---|---|---|---|
| | Mouse # | | | Mean | SD |
| | 446 | 447 | 448 | | |
| 0 (pre-dose) | BLOQ | BLOQ | BLOQ | ND | ND |
| 0.083 | 761 | 603 | 167 | 510 | 308 |
| 0.25 | 960 | 860 | 322 | 714 | 343 |
| 0.50 | 696 | 629 | 299 | 541 | 213 |
| 1.0 | 178 | 166 | 213 | 186 | 24.4 |
| 2.0 | 61.6 | 51.7 | 184 | 99.1 | 73.7 |
| 4.0 | 37.1 | 29.9 | 233 | 100 | 115 |
| 8.0 | 17.8 | 11.8 | 64.4 | 31.3 | 28.8 |
| 24 | 3.40 | 1.20 | 12.1 | 5.57 | 5.76 |
| Animal Weight (kg) | 0.032 | 0.031 | 0.034 | 0.032 | 0.002 |
| Volume Dosed (mL) | 0.48 | 0.47 | 0.51 | 0.487 | 0.021 |
| $C_{max}$ (ng/mL) | 960 | 860 | 322 | 714 | 343 |
| $t_{max}$ (hr) | 0.25 | 0.25 | 0.25 | 0.25 | 0.00 |
| $t_{1/2}$ (hr) | 6.03 | 4.45 | 5.22 | 5.24 | 0.790 |
| $MRT_{last}$ (hr) | 2.76 | 2.18 | 5.33 | 3.42 | 1.68 |
| $AUC_{last}$ (hr·ng/mL) | 1099 | 910 | 2076 | 1361 | 626 |
| $AUC_\infty$ (hr·ng/mL) | 1128 | 918 | 2167 | 1404 | 669 |
| Dose-normalized Values[1] | | | | | |
| $AUC_{last}$ (hr·kg·ng /mL/mg) | 366 | 303 | 692 | 454 | 209 |
| $AUC_\infty$ (hr·kg·ng /mL/mg) | 376 | 306 | 722 | 468 | 223 |

$C_{max}$: maximum blood concentration; $t_{max}$: time of maximum blood concentration; $t_{1/2}$: half-life, data points used for half-life determination are in bold; $MRT_{last}$: mean residence time, calculated to the last observable time point; AUClast: area under the curve, calculated to the last observable time point; $AUC_\infty$: area under the curve, extrapolated to infinity; ND: not determined; BLOQ: below the limit of quantitation (1.0 ng/mL).
[1]Dose-normalized by dividing the parameter by the nominal dose in mg/kg.

FIG. 14C

SUBSTITUTED 1,2,3,4-TETRAHYDROQUINOLINES AS INHIBITORS OF REPAIR ENZYME 8-OXOGUANINE DEOXYRIBONUCLEIC ACID GLYCOSYLASE ACTIVITY

CROSS REFERENCE TO RELATED APPLICATIONS

This application is a national stage of PCT Patent Application No. PCT/US2018/045574, entitled "Inhibitors of Base Excision Repair Activity and Therapeutic Methods Based Thereon" to Kool et al., filed Aug. 7, 2018, which claims priority to U.S. Provisional Application Ser. No. 62/683,577, filed Jun. 11, 2018, and U.S. Provisional Application Ser. No. 62/542,157, filed Aug. 7, 2017, the disclosures of which are incorporated herein by reference in their entirety.

STATEMENT REGARDING FEDERALLY SPONSORED RESEARCH

The invention described herein was made with Government support under contracts CA217809, GM067201, and GM110050 awarded by the National Institutes of Health. The Government has certain rights in the invention.

FIELD OF THE INVENTION

The invention is generally directed to compositions that inhibit repair enzyme OGG1, and biomedical research tools and therapeutics made therefrom.

BACKGROUND

The consequences of DNA damage are important to many biological pathways, and are central to mutagenesis, genotoxicity, and tumorigenesis. (See, e.g., Helleday, T., et al., R. A. *Nat. Rev. Cancer* 2008, 8, 193-204; Phillips, D. H.; Arlt, V. M. *Molecular, Clinical and Environmental Toxicology*, Springer, Basel, 2009, 87-110; Dietlei, F.; Thelen, L.; Reinhardt, H. C. *Cell Press* 2014, 326-339; Kelley, M. R.; Logsdon, D.; Fishel, M. L. *Future Oncol.* 2014, 10, 1215-1237; Gavande, N. S., et al., *Pharmacology & Therapeutics* 2016, 160, 65-83; and Chatterjee, N.; Walker, G. C. *Environ. Mol. Mutagen.* 2017, 58, 235-263, the disclosures of which are incorporated herein by reference.) Among the most frequent forms of damage in DNA is 8-oxoguanine (8-OG), which is generated by reactive oxygen species arising from metabolism, or exposure to agents that induce oxidative stress. (See, e.g., Kasai, Hiroshi; Nishimura, S. *Nucleic Acids Res.* 1984, 12, 2137-2145; Dizdaroglu, M. *Biochem J.* 1986, 238, 247-254; Kasai, H.; Nishimura, S. *Environ. Health Perspect.* 1986, 67, 111-116; Kasai, H; Crain, P. F.; Kuchino, Y., et al. *Carcinogenesis* 1986, 11, 1849-1851; Kasai, H.; Nishimura, S.; Kurokawa, Y.; Hayashi, Y. *Carcinogenesis* 1987, 8, 1959-1961; Ames, B. N.; Gold, L. S. *Mutation Research* 1991, 250, 3-16; Abu-Shakra, A.; Zeiger, E. *Mutation Research* 1997, 390, 45-50; Cadet, J.; Douki, T.; Gasparutto, D.; Ravanat, J.-L. *Mutation Research* 2003, 531, 5-23; Bont, R. D.; van Larebeke, N. *Mutagenesis* 2004, 19, 169-185; Singh, S. K., et al., *Nucleic Acids Res.* 2011, 39, 6789-6801; and Nakabeppu, Y. *Int. J. Mol. Sci.* 2014, 15, 12543-12557, the disclosures of which are incorporated herein by reference.) Because 8-OG is mispaired frequently with adenine during DNA replication, it is highly mutagenic, and the frequency of guanine oxidation combined with this mispairing causes it to be the greatest single source of mutations in the cell. (See, e.g., Shibutani, S.; Takeshita, M.; Grollman, A. P. *Nature* 1991, 349, 431-434, the disclosure of which is incorporated herein by reference.) Mutations that occur in proto-oncogenes can initiate tumorigenesis, and the presence of 8-OG in DNA can also be harmful to cell growth by leading to DNA double strand breaks. (See, e.g., Anderson, M. W., et al., *Environ. Health Pespect.* 1992, 98, 13-24; and Kozmin, S. G., et al., *Nucleic Acids Res.* 2009, 37, 1767-1777, the disclosures of which are incorporated herein by reference.)

SUMMARY OF THE INVENTION

In many embodiments, the invention is directed to small molecules that inhibit repair enzyme 8-oxoguanine DNA glycosylase (OGG1), biomedical research tools and therapeutics made therefrom, and assays for identifying such small molecule inhibitors.

In some embodiments the OGG1 inhibitor includes a molecule of formula:

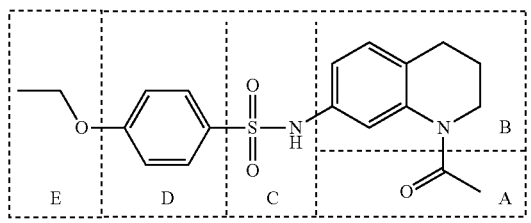

where A may be substituted in accordance with the formula:

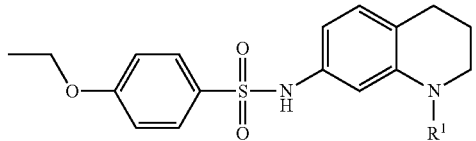

where $R^1$ may be selected from the list consisting of:
hydrogen, deuterium, a Group 1 moiety, a Group 2 moiety, a Group 3, moiety, a Group 4 moiety, a Group 5 moiety, a Group 6 moiety, a Group 7 moiety, and a Group 8 moiety where a Group 1 moiety has 1 to 4 carbon atoms and is selected from the group consisting of: alkyls, cycloalkylalkyls, aryls, and arylalkyls, and combinations thereof, where a Group 2 moiety is a moiety selected from Group 1 where one or more carbon atoms not connected to the nitrogen atom on B is substituted by an atom selected from the group consisting of: O, S, N, Si, P, and B, or any combination thereof, wherein where a N, P or B atom is selected the atom may be further substituted with one or more functionalities selected from the group of —H, —OH, —OR, and —R, wherein R is a moiety selected from Group 1, wherein a Group 3 moiety is a moiety selected from Group 1 or Group 2, wherein one or more hydrogen atoms are substituted with one of functionalities selected from the group consisting of: —OR, —NR$_2$, —ONO$_2$, —CN, —N$_3$, —NO$_2$, —SR, —SO$_2$R, —SO₃R, —SCN, —NCS, —OP(O)(OR)₂, and —B(OR)₂, wherein every R is either a H or a moiety selected from Group 1, where a Group 4 moiety is a moiety selected from one of Group 1, Group 2, or Group 3, wherein one or more hydrogen atoms are replaced with one of either a halogen atom or a deuterium atom, where a Group 5 moiety is —C(O)R$^{10}$, wherein R$^{10}$ is a moiety selected from one of Group 1, Group 2, Group 3, or Group 4, where a Group 6 moiety is —C(O)N(H)R$^{11}$, wherein R$^{11}$ is a moiety selected from one of Group 1, Group 2, Group 3, or Group 4, where a Group 7 moiety is —C(O)N(R$^{12}$)R$^{13}$, wherein R$^{12}$ and R$^{13}$ are each moieties independently selected from one of Group 1, Group 2, Group 3, or Group 4, and where a Group 8 moiety is —S(O)₂R$^{14}$, wherein R$^{14}$ is a moiety selected from one of Group 1, Group 2, Group 3, or Group 4;

where B is a tetrahydroquinoline wherein the hydrogen atoms of the tetrahydroquinoline may be replaced with one or more moieties selected from the group consisting of: deuterium, halogen, alkyl, hydroxyl, amino, and alkoxy/alkylamino;

where C is a sulfonamide wherein the hydrogen atom on the amide may be substituted with a moiety selected from one of either hydroxyl (—OH) or 3-acetyl;

where D may be substituted in accordance with the formula:

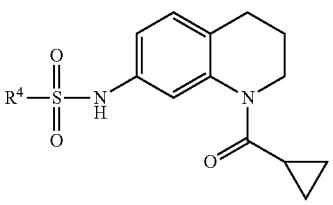

where R$^4$ is an aryl or heteroaryl, optionally substituted at any position with one or more moieties selected from the group consisting of: alkyls, haloalkyls, or any combination thereof, halogens, deuteriums, —OR, —SR—NR₂, —OCN, —NCO, —ONO₂, —CN, —NC, —N₃, —NO₂, —SR, —SO₂R, —SO₃R, —SCN, —NCS, —OP(O)(OR)₂, —B(OR)₂; —C(═O)R, —C(═O)OR, —OC(═O)R, —C(═O)NR₂, OC(═O)NR₂, —NRC(═O)R, NRC(═O)OR, —NRC(═O)NR₂, —NRS(═O)₂R, —NRS(═O)₂NR₂, —S(═O)R, —S(═O)₂R and —S(═O)₂NR₂, wherein each R is independently selected from the group consisting of: H, saturated or unsaturated hydrocarbons, and halogenated hydrocarbons, wherein independent R groups can optionally be joined to form cyclic structures; and where E may be substituted in accordance with the formula:

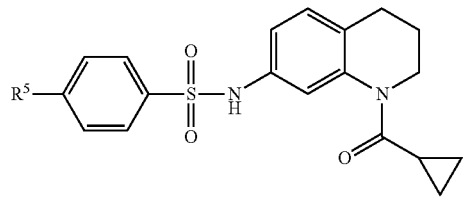

where R$^5$ is a moiety selected from the group consisting of: hydrogen, deuterium, halogen, alkyl, cycloalkyl, alkenyl, alkynyl, aryl, heteroaryl, heterocycloalkyl; —OR, —SR—NR₂, —OCN, —NCO, —ONO₂, —CN, —NC, —N₃, —NO₂, —SR, —SO₂R, —SO₃R, —SCN, —NCS, —OP(O)(OR)₂, —B(OR)₂; —C(═O)R, —C(═O)OR, —OC(═O)R, —C(═O)NR₂, OC(═O)NR₂, —NRC(═O)R, NRC(═O)OR, —NRC(═O)NR₂, —NRS(═O)₂R, —NRS(═O)₂NR₂, —S(═O)R, —S(═O)₂R and —S(═O)₂NR₂, wherein each R is independently selected from the group consisting of: H, saturated or unsaturated hydrocarbons, and halogenated hydrocarbons, wherein independent R groups can optionally be joined to form cyclic structures.

In a further embodiment, R1 is a chain or ringed moiety of C4 or less, B is a closed or open-ringed tetrahydroquinoline, C is a sulfonamide, iminosulfonamide, or phosphonamide, having an amide nitrogen substitution selected from N—H, N-D, N—OH, or N-methyl attached thereto, R4 is a single or multi-ringed substituted or unsubstituted aromatic, and R5 is a substituted or unsubstituted aromatic having a polar and electron-donating group disposed at either position 3 or 4 on the terminal aromatic ring of R4.

In another embodiment, R$^1$ is selected from the group consisting of an acetamide, an ethylamide, a cyclopropylamide, and a cyclobutamide.

In a still further embodiment, C and D jointly comprise a benzenesulfonamide.

In still another embodiment, R$^4$ is selected from the group consisting of a phenyl, a diphenyl, a diphenyl ether, a cyclohexylphenyl, a pyrazolylphenyl, and a pyridylphenyl.

In a yet further embodiment, R$^5$ is selected from the group consisting of a phenyl, a diphenyl, a diphenyl ether, a cyclohexylphenyl, a pyrazolylphenyl, and a pyridylphenyl, having a substituent selected from the group consisting of a methoxy, a dimethylamino, an acetylamino, a carboxamino, and a meta-carboxamide.

In yet another embodiment, a method of synthesizing an OGG1 inhibitor includes:

combining 7-Nitro-1,2,3,4-tetrahydroquinoline with acyl chloride, to form a crude product having structure:

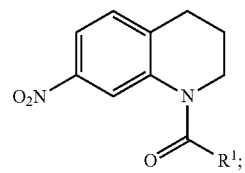

hydrogenating the crude product to form a product having the structure:

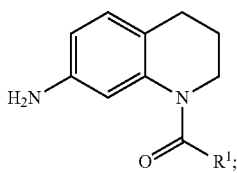

combining the product with sulfonyl chloride to form an end product having formula:

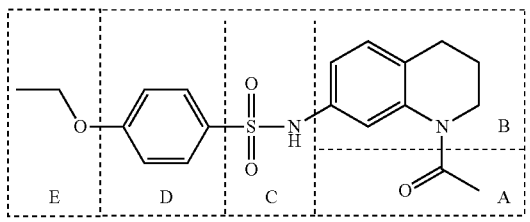

where A may be substituted in accordance with the formula:

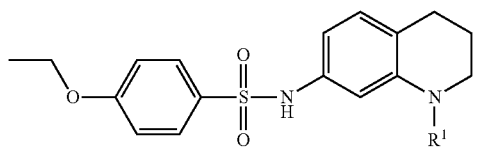

where $R^1$ may be selected from the list consisting of hydrogen, deuterium, a Group 1 moiety, a Group 2 moiety, a Group 3, moiety, a Group 4 moiety, a Group 5 moiety, a Group 6 moiety, a Group 7 moiety, and a Group 8 moiety;
- where a Group 1 moiety has 1 to 4 carbon atoms and is selected from the group consisting of: alkyls, cycloalkylalkyls, aryls, and arylalkyls, and combinations thereof,
- where a Group 2 moiety is a moiety selected from Group 1 wherein one or more carbon atoms not connected to the nitrogen atom on B is substituted by an atom selected from the group consisting of: O, S, N, Si, P, and B, or any combination thereof, wherein where a N, P or B atom is selected the atom may be further substituted with one or more functionalities selected from the group of —H, —OH, —OR, and —R, wherein R is a moiety selected from Group 1,
- where a Group 3 moiety is a moiety selected from Group 1 or Group 2, wherein one or more hydrogen atoms are substituted with one of functionalities selected from the group consisting of: —OR, —NR$_2$, —ONO$_2$, —CN, —N$_3$, —NO$_2$, —SR, —SO$_2$R, —SO$_3$R, —SCN, —NCS, —OP(O)(OR)$_2$, and —B(OR)$_2$, wherein every R is either a H or a moiety selected from Group 1,
- where a Group 4 moiety is a moiety selected from one of Group 1, Group 2, or Group 3, wherein one or more hydrogen atoms are replaced with one of either a halogen atom or a deuterium atom,
- where a Group 5 moiety is —C(O)R$^{10}$, wherein R$^{10}$ is a moiety selected from one of Group 1, Group 2, Group 3, or Group 4,
- where a Group 6 moiety is —C(O)N(H)R$^{11}$, wherein R$^{11}$ is a moiety selected from one of Group 1, Group 2, Group 3, or Group 4,
- where a Group 7 moiety is —C(O)N(R$^{12}$)R$^{13}$, wherein R$^{12}$ and R$^{13}$ are each moieties independently selected from one of Group 1, Group 2, Group 3, or Group 4, and
- where a Group 8 moiety is —S(O)$_2$R$^{14}$, wherein R$^{14}$ is a moiety selected from one of Group 1, Group 2, Group 3, or Group 4;

where B is a tetrahydroquinoline wherein the hydrogen atoms of the tetrahydroquinoline may be replaced with one or more moieties selected from the group consisting of: deuterium, halogen, alkyl, hydroxyl, amino, and alkoxy/alkylamino;

where C is a sulfonamide wherein the hydrogen atom on the amide may be substituted with a moiety selected from one of either hydroxyl (—OH) or $C_{1-3}$-acetyl;

where D may be substituted in accordance with the formula:

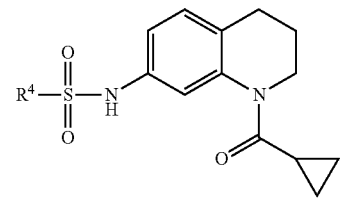

where $R^4$ is an aryl or heteroaryl, optionally substituted at any position with one or more moieties selected from the group consisting of: alkyls, haloalkyls, or any combination thereof, halogens, deuteriums, —OR, —SR—NR$_2$, —OCN, —NCO, —ONO$_2$, —CN, —NC, —N$_3$, —NO$_2$, —SR, —SO$_2$R, —SO$_3$R, —SCN, —NCS, —OP(O)(OR)$_2$, —B(OR)$_2$; —C(=O)R, —C(=O)OR, —OC(=O)R, —C(=O)NR$_2$, OC(=O)NR$_2$, —NRC(=O)R, NRC(=O)OR, —NRC(=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures; and where E may be substituted in accordance with the formula:

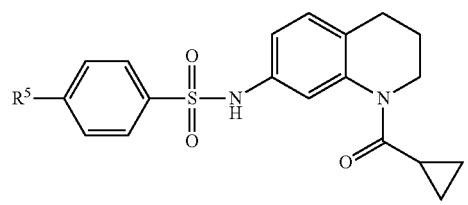

where $R^5$ is a moiety selected from the group consisting of: hydrogen, deuterium, halogen, alkyl, cycloalkyl, alkenyl, alkynyl, aryl, heteroaryl, heterocycloalkyl; —OR, —SR—NR$_2$, —OCN, —NCO, —ONO$_2$, —CN, —NC, —N$_3$, —NO$_2$, —SR, —SO$_2$R, —SO$_3$R, —SCN, —NCS, —OP(O)(OR)$_2$, —B(OR)$_2$; —C(=O)R, —C(=O)OR, —OC(=O)

R, —C(=O)NR$_2$, OC(=O)NR$_2$, —NRC(=O)R, NRC(=O)OR, —NRC(=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures.

In a further embodiment again, the combining the 7-Nitro-1,2,3,4-tetrahydroquinoline with the acyl chloride step includes the steps of dissolving the 7-Nitro-1,2,3,4-tetrahydroquinoline in dichloromethane and adding the acyl chloride and N,N-diisopropylethylamine.

In another embodiment again, the combining the 7-Nitro-1,2,3,4-tetrahydroquinoline with the acyl chloride step further includes the steps of removing the dicholoromethane under reduced pressure, adding ethyl acetate and water to the crude product, washing the crude product with water and brine, and drying the crude product with magnesium sulfate.

In a further additional embodiment, the hydrogenating step includes the steps of dissolving the crude product in methanol and dicholoromethane, adding a catalyst to hydrogenate the crude product, wherein the catalyst is selected from the group consisting of palladium on carbon and palladium hydroxide on carbon, degassing the crude product with argon, and introducing hydrogen gas.

In another additional embodiment, the combining the product with the sulfonyl chloride step includes the steps of dissolving the product in dry pyrimidine and dicholoromethane, cooling the product with an ice bath, and adding the sulfonyl chloride.

In a still yet further embodiment, the combining the product with the sulfonyl chloride step further includes the steps of adding ethyl acetate to the end product, washing the end product with hydrochloric acid and brine, drying the end product with magnesium sulfate, removing the ethyl acetate under reduced pressure, and purifying the end product, where the purification is accomplished by at least one of the group consisting of crystallization and silica gel column chromatography.

In still yet another embodiment, R1 is a chain or ringed moiety of C4 or less, B is a closed or open-ringed tetrahydroquinoline, C is a sulfonamide, iminosulfonamide, or phosphonamide, having an amide nitrogen substitution selected from N—H, N-D, N—OH, or N-methyl attached thereto, R4 is a single or multi-ringed substituted or unsubstituted aromatic, and R5 is a substituted or unsubstituted aromatic having a polar and electron-donating group disposed at either position 3 or 4 on the terminal aromatic ring of R4.

In a still further embodiment again, R1 is selected from the group consisting of an acetamide, an ethylamide, a cyclopropylamide, and a cyclobutamide.

In still another embodiment again, C and D jointly comprise a benzenesulfonamide.

In a still further additional embodiment, R4 is selected from the group consisting of a phenyl, a diphenyl, a diphenyl ether, a cyclohexylphenyl, a pyrazolylphenyl, and a pyridylphenyl.

In still another additional embodiment, R5 is selected from the group consisting of a phenyl, a diphenyl, a diphenyl ether, a cyclohexylphenyl, a pyrazolylphenyl, and a pyridylphenyl, having a substituent selected from the group consisting of a methoxy, a dimethylamino, an acetylamino, a carboxamino, and a meta-carboxamide.

In a yet further embodiment again, a therapeutic formulation of an OGG1 inhibitor includes: a pharmaceutical excipient and an OGG1 inhibitor comprising a molecule of formula:

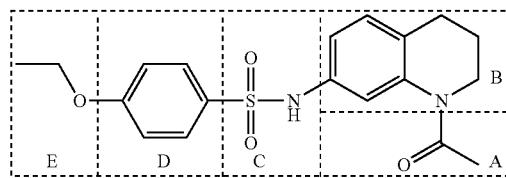

where A may be substituted in accordance with the formula:

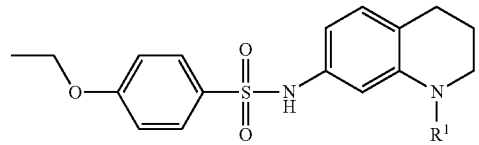

where $R^1$ may be selected from the list consisting of hydrogen, deuterium, a Group 1 moiety, a Group 2 moiety, a Group 3, moiety, a Group 4 moiety, a Group 5 moiety, a Group 6 moiety, a Group 7 moiety, and a Group 8 moiety;
where a Group 1 moiety has 1 to 4 carbon atoms and is selected from the group consisting of: alkyls, cycloalkylalkyls, aryls, and arylalkyls, and combinations thereof,
where a Group 2 moiety is a moiety selected from Group 1 wherein one or more carbon atoms not connected to the nitrogen atom on B is substituted by an atom selected from the group consisting of: O, S, N, Si, P, and B, or any combination thereof, wherein where a N, P or B atom is selected the atom may be further substituted with one or more functionalities selected from the group of —H, —OH, —OR, and —R, wherein R is a moiety selected from Group 1,
where a Group 3 moiety is a moiety selected from Group 1 or Group 2, wherein one or more hydrogen atoms are substituted with one of functionalities selected from the group consisting of: —OR, —NR$_2$, —ONO$_2$, —CN, —N$_3$, —NO$_2$, —SR, —SO$_2$R, —SO$_3$R, —SCN, —NCS, —OP(O)(OR)$_2$, and —B(OR)$_2$, wherein every R is either a H or a moiety selected from Group 1,
where a Group 4 moiety is a moiety selected from one of Group 1, Group 2, or Group 3, wherein one or more hydrogen atoms are replaced with one of either a halogen atom or a deuterium atom,
where a Group 5 moiety is —C(O)R$^{10}$, wherein R$^{10}$ is a moiety selected from one of Group 1, Group 2, Group 3, or Group 4,
where a Group 6 moiety is —C(O)N(H)R$^{11}$, wherein R$^{11}$ is a moiety selected from one of Group 1, Group 2, Group 3, or Group 4,
where a Group 7 moiety is —C(O)N(R$^{12}$)R$^{13}$, wherein R$^{12}$ and R$^{13}$ are each moieties independently selected from one of Group 1, Group 2, Group 3, or Group 4, and
where a Group 8 moiety is —S(O)$_2$R$^{14}$, wherein R$^{14}$ is a moiety selected from one of Group 1, Group 2, Group 3, or Group 4;

where B is a tetrahydroquinoline wherein the hydrogen atoms of the tetrahydroquinoline may be replaced with one or more moieties selected from the group consisting of: deuterium, halogen, alkyl, hydroxyl, amino, and alkoxy/alkylamino;

where C is a sulfonamide wherein the hydrogen atom on the amide may be substituted with a moiety selected from one of either hydroxyl (—OH) or $C_{1-3}$-acetyl;

where D may be substituted in accordance with the formula:

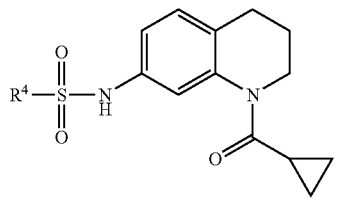

where $R^4$ is an aryl or heteroaryl, optionally substituted at any position with one or more moieties selected from the group consisting of: alkyls, haloalkyls, or any combination thereof, halogens, deuteriums, —OR, —SR—$NR_2$, —OCN, —NCO, —$ONO_2$, —CN, —NC, —$N_3$, —$NO_2$, —SR, —$SO_2R$, —$SO_3R$, —SCN, —NCS, —OP(O)(OR)$_2$, —B(OR)$_2$; —C(=O)R, —C(=O)OR, —OC(=O)R, —C(=O)NR$_2$, OC(=O)NR$_2$, —NRC(=O)R, NRC(=O)OR, —NRC(=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures; and where E may be substituted in accordance with the formula:

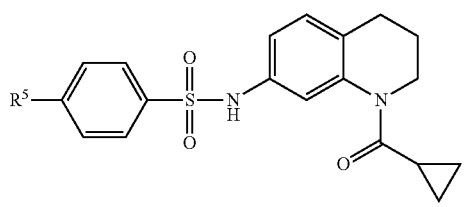

where $R^5$ is a moiety selected from the group consisting of: hydrogen, deuterium, halogen, alkyl, cycloalkyl, alkenyl, alkynyl, aryl, heteroaryl, heterocycloalkyl; —OR, —SR—NR$_2$, —OCN, —NCO, —ONO$_2$, —CN, —NC, —N$_3$, —NO$_2$, —SR, —SO$_2$R, —SO$_3$R, —SCN, —NCS, —OP(O)(OR)$_2$, —B(OR)$_2$; —C(=O)R, —C(=O)OR, —OC(=O)R, —C(=O)NR$_2$, OC(=O)NR$_2$, —NRC(=O)R, NRC(=O)OR, —NRC(=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures.

In yet another embodiment again, R1 is a chain or ringed moiety of C4 or less, B is a closed or open-ringed tetrahydroquinoline, C is a sulfonamide, iminosulfonamide, or phosphonamide, having an amide nitrogen substitution selected from N—H, N-D, N—OH, or N-methyl attached thereto, R4 is a single or multi-ringed substituted or unsubstituted aromatic, and R5 is a substituted or unsubstituted aromatic having a polar and electron-donating group disposed at either position 3 or 4 on the terminal aromatic ring of R4.

In a yet further additional embodiment, R1 is selected from the group consisting of an acetamide, an ethylamide, a cyclopropylamide, and a cyclobutamide.

In yet another additional embodiment, C and D jointly comprise a benzenesulfonamide.

In a further additional embodiment again, R4 is selected from the group consisting of a phenyl, a diphenyl, a diphenyl ether, a cyclohexylphenyl, a pyrazolylphenyl, and a pyridylphenyl.

In another additional embodiment again, R5 is selected from the group consisting of a phenyl, a diphenyl, a diphenyl ether, a cyclohexylphenyl, a pyrazolylphenyl, and a pyridylphenyl, having a substituent selected from the group consisting of a methoxy, a dimethylamino, an acetylamino, a carboxamino, and a meta-carboxamide.

In another further additional embodiment, the pharmaceutical excipient is at least one of the group consisting of a filler, a disentegrant, a lubricant, a glidant, a binder, and a buffer.

In a still yet further embodiment again, a method of treating an individual with an OGG1 inhibitor includes obtaining a therapeutically effective amount of the OGG1 inhibitor and administering the therapeutically effective amount of the OGG1 inhibitor to the individual.

In still yet another embodiment again, the therapeutically effective amount of the OGG1 inhibitor is a pharmaceutical formulation comprising the OGG1 inhibitor and a pharmaceutical excipient.

In a still yet further additional embodiment, the pharmaceutical excipient is at least one of the group consisting of a filler, a disentegrant, a lubricant, a glidant, a binder, and a buffer.

In still yet another additional embodiment, the administering step is performed by intraperitoneal injection.

In a yet further additional embodiment again, the OGG1 inhibitor comprises a molecule of formula:

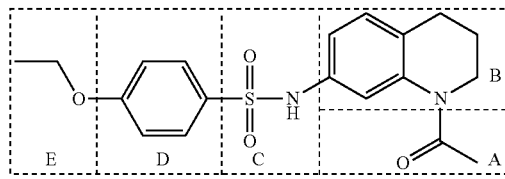

where A may be substituted in accordance with the formula:

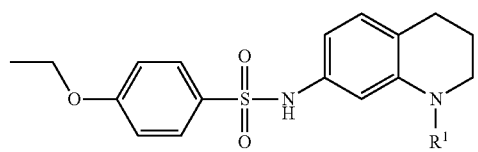

where $R^1$ may be selected from the list consisting of hydrogen, deuterium, a Group 1 moiety, a Group 2 moiety, a Group 3, moiety, a Group 4 moiety, a Group 5 moiety, a Group 6 moiety, a Group 7 moiety, and a Group 8 moiety;

where a Group 1 moiety has 1 to 4 carbon atoms and is selected from the group consisting of: alkyls, cycloalkylalkyls, aryls, and arylalkyls, and combinations thereof, where a Group 2 moiety is a moiety selected from Group 1 wherein one or more carbon atoms not connected to the nitrogen atom on B is substituted by an atom selected from the group consisting of: O, S, N, Si, P, and B, or any combination thereof, wherein where a N, P or B atom is selected the atom may be further substituted with one or more functionalities selected from the group of —H, —OH, —OR, and —R, wherein R is a moiety selected from Group 1, where a Group 3 moiety is a moiety selected from Group 1 or Group 2, wherein one or more hydrogen atoms are substituted with one of functionalities selected from the group consisting of: —OR, —NR$_2$, —ONO$_2$, —CN, —N$_3$, —NO$_2$, —SR, —SO$_2$R, —SO$_3$R, —SCN, —NCS, —OP(O)(OR)$_2$, and —B(OR)$_2$, wherein every R is either a H or a moiety selected from Group 1, where a Group 4 moiety is a moiety selected from one of Group 1, Group 2, or Group 3, wherein one or more hydrogen atoms are replaced with one of either a halogen atom or a deuterium atom, where a Group 5 moiety is —C(O)R$^{10}$, wherein R$^{10}$ is a moiety selected from one of Group 1, Group 2, Group 3, or Group 4, where a Group 6 moiety is —C(O)N(H)R$^{11}$, wherein R$^{11}$ is a moiety selected from one of Group 1, Group 2, Group 3, or Group 4, where a Group 7 moiety is —C(O)N(R$^{12}$)R$^{13}$, wherein R$^{12}$ and R$^{13}$ are each moieties independently selected from one of Group 1, Group 2, Group 3, or Group 4, and where a Group 8 moiety is —S(O)$_2$R$^{14}$, wherein R$^{14}$ is a moiety selected from one of Group 1, Group 2, Group 3, or Group 4;

where B is a tetrahydroquinoline wherein the hydrogen atoms of the tetrahydroquinoline may be replaced with one or more moieties selected from the group consisting of: deuterium, halogen, alkyl, hydroxyl, amino, and alkoxy/alkylamino;

where C is a sulfonamide wherein the hydrogen atom on the amide may be substituted with a moiety selected from one of either hydroxyl (—OH) or C$_{1-3}$-acetyl;

where D may be substituted in accordance with the formula:

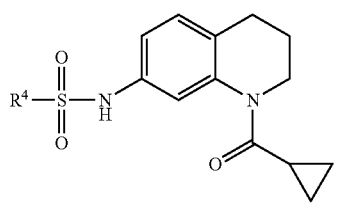

where R$^4$ is an aryl or heteroaryl, optionally substituted at any position with one or more moieties selected from the group consisting of: alkyls, haloalkyls, or any combination thereof, halogens, deuteriums, —OR, —SR—NR$_2$, —OCN, —NCO, —ONO$_2$, —CN, —NC, —N$_3$, —NO$_2$, —SR, —SO$_2$R, —SO$_3$R, —SCN, —NCS, —OP(O)(OR)$_2$, —B(OR)$_2$; —C(=O)R, —C(=O)OR, —OC(=O) R, —C(=O)NR$_2$, OC(=O)NR$_2$, —NRC(=O)R, NRC(=O)OR, —NRC(=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures; and where E may be substituted in accordance with the formula:

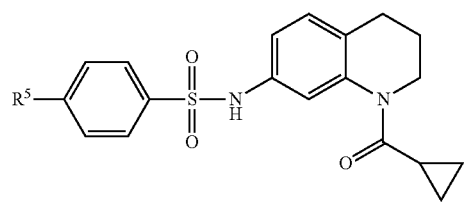

where R$^5$ is a moiety selected from the group consisting of: hydrogen, deuterium, halogen, alkyl, cycloalkyl, alkenyl, alkynyl, aryl, heteroaryl, heterocycloalkyl; —OR, —SR—NR$_2$, —OCN, —NCO, —ONO$_2$, —CN, —NC, —N$_3$, —NO$_2$, —SR, —SO$_2$R, —SO$_3$R, —SCN, —NCS, —OP(O)(OR)$_2$, —B(OR)$_2$; —C(=O) R, —C(=O)OR, —OC(=O)R, —C(=O)NR$_2$, OC(=O)NR$_2$, —NRC(=O)R, NRC(=O)OR, —NRC (=O)NR$_2$, —NRS(=O)$_2$R, —NRS(=O)$_2$NR$_2$, —S(=O)R, —S(=O)$_2$R and —S(=O)$_2$NR$_2$, wherein each R is independently selected from the group consisting of: H, saturated or unsaturated hydrocarbons, and halogenated hydrocarbons, wherein independent R groups can optionally be joined to form cyclic structures.

In yet another additional embodiment again, R1 is a chain or ringed moiety of C4 or less, B is a closed or open-ringed tetrahydroquinoline, C is a sulfonamide, iminosulfonamide, or phosphonamide, having an amide nitrogen substitution selected from N—H, N-D, N—OH, or N-methyl attached thereto, R4 is a single or multi-ringed substituted or unsubstituted aromatic, and R5 is a substituted or unsubstituted aromatic having a polar and electron-donating group disposed at either position 3 or 4 on the terminal aromatic ring of R4.

In a still yet further additional embodiment again, R1 is selected from the group consisting of an acetamide, an ethylamide, a cyclopropylamide, and a cyclobutamide.

In still yet another additional embodiment again, C and D jointly comprise a benzenesulfonamide.

In another further embodiment, R4 is selected from the group consisting of a phenyl, a diphenyl, a diphenyl ether, a cyclohexylphenyl, a pyrazolylphenyl, and a pyridylphenyl.

In still another further embodiment, R5 is selected from the group consisting of a phenyl, a diphenyl, a diphenyl ether, a cyclohexylphenyl, a pyrazolylphenyl, and a pyridylphenyl, having a substituent selected from the group consisting of a methoxy, a dimethylamino, an acetylamino, a carboxamino, and a meta-carboxamide.

Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

FIGS. 2A-2B provide flow charts of a method of developing OGG1 inhibitors according to embodiments.

FIGS. 4A-4M provide diagrams OGG1 inhibitors according to embodiments.

FIGS. 14A-14C provide data for OGG1 inhibitor stability in mice in according to embodiments.

DETAILED DESCRIPTION

Figure 1:
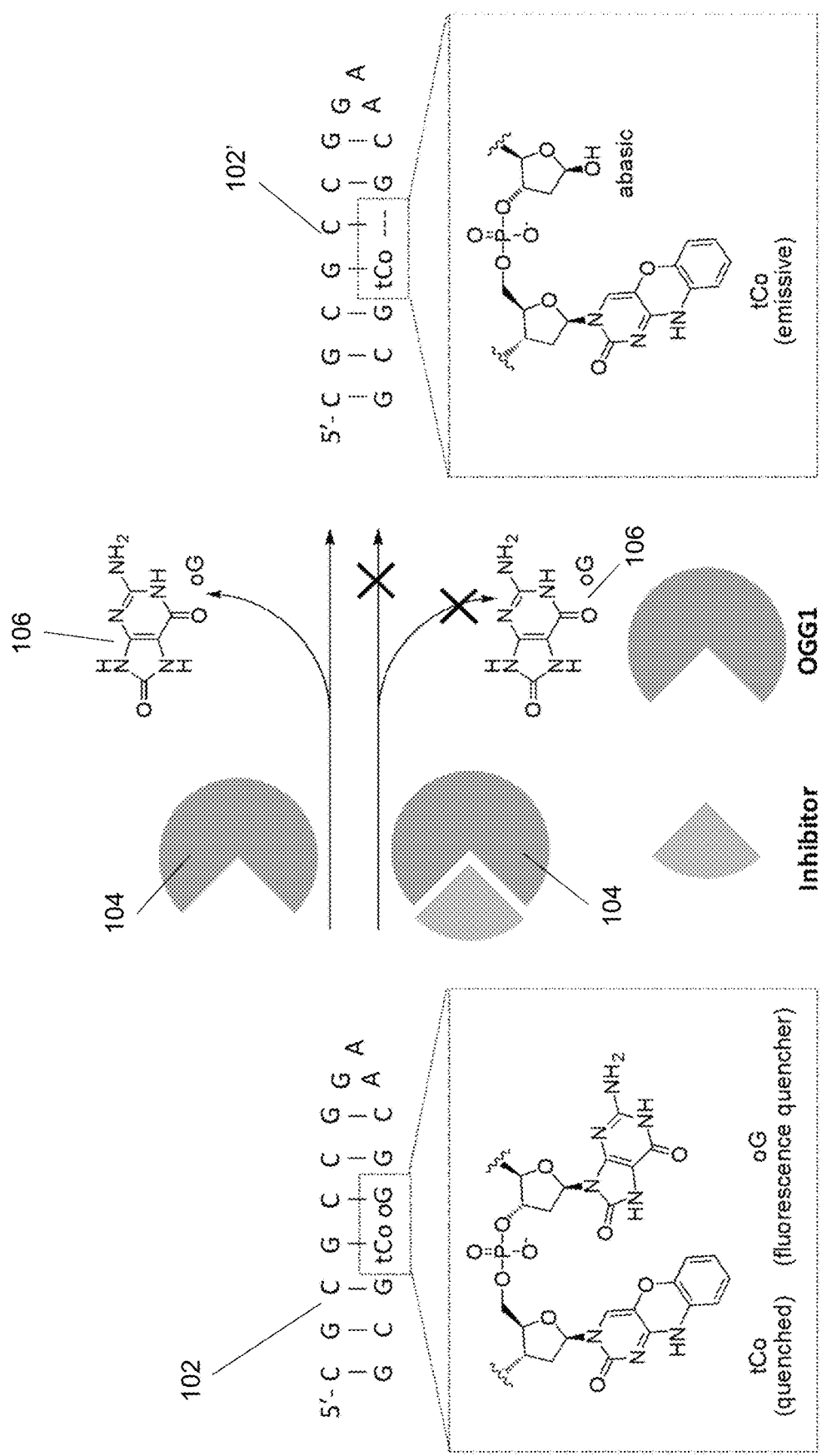
FIG. 1 provides diagrams of a probe for an OGG1 assay according to embodiments.

Turning now to the drawings and data, noncovalent small-molecule inhibitors of DNA repair enzyme 8-oxoguanine DNA glycosylase (OGG1), methods for their production, assays for screening such inhibitors, and therapeutics using such inhibitors are provided. Many embodiments of the inhibitors are directed to derivatives of a tetrahydroquinoline, including, for example, am idobiphenyls. In various embodiments, small molecules in accordance with embodiments selectively inhibit OGG1 over multiple repair enzymes. Some embodiments are directed to tools for studying and therapeutics for treating disease pathways related to OGG1.

Overview of OGG1 Activity in Disease Pathways

The primary enzyme for repairing 8-oxoguanine (8-OG) in DNA is 8-oxoguanine DNA glycosylase (OGG1), which functions via a base excision repair (BER) mechanism. (See, e.g., Lu, R.; Nash, H. M.; Verdine, G. L. *Curr. Biol.* 1997, 7, 397-407, the disclosure of which is incorporated herein by reference.) The enzyme exists both in the nucleus and mitochondria, repairing DNA damage in both subcellular locations. (See, e.g., Nakabeppu, Y. *Prog. Nucleic Acid Res. Mol. Biol.* 2001, 68, 75-94, the disclosures of which is incorporated herein by reference.) It recognizes 8-OG in double-stranded DNA, and cleaves the glycosidic bond, releasing the 8-OG free base, and generating an abasic deoxyribose in the DNA. This abasic site is then further processed by lyase activities of the enzyme itself or the AP lyase enzyme, ultimately leading to strand cleavage. (See, e.g., Bauer, N. C.; Corbett, A. H.; Doetsch, P. W. *Nucleic Acids Res.* 2015, 43, 10083-10101; and Zhang, Y.; Rohde, Larry, H.; Wu, H. *Current Genomics* 2009, 10, 250-258, the disclosures of which are incorporated herein by reference.) Additional enzymes in the BER pathway can then complete the damage repair, regenerating intact DNA with correctly paired bases. (See, Le, R., et al., *Curr. Biol.* 1997, cited above.)

Because of the importance of OGG1 to DNA mutations and genotoxicity, a good deal of study has been devoted to investigating how varied levels of this activity can affect disease pathologies. OGG1-deficient mice display elevated levels of genomic 8-oxoguanine and increased mutations, highlighting the importance of this enzyme in maintaining genome integrity. (See, e.g., Klungland, A., et al., *Proc. Natl. Acad. Sci. USA* 1999, 96, 13300-133050GG1; and Osterod, M., et al., *Carcinogenesis* 2001, 22, 1459-1463, the disclosures of which are incorporated herein by reference.) OGG1 mutants with abolished or decreased 8-OG repair activity have been found in many cancer specimens. (See, e.g., Mahjabeen, I., et al., *Tumor Biol.* 2014, 35, 5971-5983A; and Ali, K., et al., *Dis. Markers,* 2015, 690878, the disclosures of which are incorporated herein by reference.) A common OGG1 polymorphism, S126C, which lowers BER activity, is positively associated with frequency of cancers of the digestive system and the lung. (See, e.g., Sugimura, H., et al., *Cancer Epidemiol. Biomarkers Prev.* 1999, 8, 669-674; Zhong, D., et al., *Sci. Rep.* 2012, 2, 548; and Das, S., et al., *Springerplus.* 2016, 29, 227, the disclosures of which are incorporated herein by reference.) In addition to its prominent association with genetic mutations leading to malignancies, OGG1-mediated repair of 8-oxoguanine has been associated with inflammation-related pathologies as well. (See, e.g., Bacsi, A., et al., *DNA Repair* 2013, 12, 18-26, the disclosure of which is incorporated herein by reference.) 8-OG is known to act as a signaling molecule that modulates activity of several GTPases. (See, e.g., Aguilera-Aguirre, L., et al., *J. Immunol.* 2014, 193, 4643-4653, the disclosure of which is incorporated herein by reference.) Downregulated OGG1 activity results in decreased lung inflammation in murine allergy models, and polymorphisms in the OGG1 gene have been associated with rheumatoid arthritis. (See, e.g., Chen, S. Y., et al., *Rheumatol. Int.* 2012, 32, 1165-1169, the disclosure of which is incorporated herein by reference.)

Taken together, the data suggest strong links between OGG1 and multiple disease states. Accordingly, it would be desirable to have small molecule inhibitors of the enzyme, which could be useful as tools to study OGG1-related pathways and pathologies in cellular and animal models, and also as potential therapeutics. Previous small molecule inhibitors of OGG1 were reported recently, which described simple hydrazine and hydrazone derivatives that inhibited the enzyme as measured by an assay that measures DNA strand cleavage subsequent to base excision. (See, e.g., Donley, N., et al., *ACS Chem. Biol.* 2015, 10, 2334-2343, the disclosure of which is incorporated herein by reference.) Since hydrazones can spontaneously hydrolyze, and hydrazines are known to react generally with abasic sites in DNA, such classes of compounds may raise questions of stability and specificity. (See, e.g., Testa, B.; Mayer, J. M. *Hydrolysis in Drug and Prodrug Metabolism Chemistry, biochemistry and enzymology*, Wiley-VCH, Weinheim, 2003, Chapter 4, 148-162; Sugiyama, H., et al., *J. Am. Chem. Soc.* 1990, 112, 5252-5257; and Chowdhury, G.; Guengerich, F. P. *Chem. Res. Toxicol.* 2009, 22, 1310-1319, the disclosures of which are incorporated herein by reference.) In general, the use of base excision repair (BER) assays that measure DNA cleavage rather than the excision event may result in identification of hit compounds that do not act by inhibiting initial base excision.

Embodiments of OGG1 Inhibitor Assays

In view of the deficiencies with conventional assays and inhibitors, many embodiments are directed to assays that directly measure excision by OGG1. In various embodiments, the assay incorporates a fluorogenic probe (OGR1) configured to directly measure the base excision activity of OGG1 by detecting the excision of 8-OG in real-time (FIG. 1). (See, e.g., Edwards, S. K., et al., *ChemBioChem* 2015, 16, 1637-1646, the disclosure of which is incorporate herein by reference.) In embodiments of this probe, 8-OG acts as a fluorescence quencher of a neighboring fluorescent DNA base, and enzymatic excision of the 8-OG renders the probe emissive. In various other embodiments, fluorescence intensity increases may be used to supply quantitative assays of OGG1 activity.

FIG. 1 illustrates the process of assays to measure inhibition of OGG1. In this figure, the probe OGR1 102 forms a hairpin structure. This probe contains 1,3-diaza-2-oxophenoxazine and 8-OG represented by tCo and oG, respectively. The substituted base, tCo, is a fluorescent base analog with an emission frequency that is quenched by 8-OG. In an intact OGR1 102, 8-OG quenches the fluorescence of tCo. Without inhibition, OGG1 104 will excise the 8-OG 106 from OGR1 and release the 8-OG 106 into solution. By releasing the 8-OG 106 into solution, the OGR1 102' will now possess and abasic ribose, which will allow tCo emission, because 8-OG will no longer quench the fluorescence. This fluorescence can be measured as an indication of OGG1 activity.

However, in the presence of an inhibitor 108, OGG1 104 will no longer excise 8-OG from OGR1. During inhibition, an inhibitor 108 can interact with OGG1 104, which prevents OGG1 104 from excising 8-OG 106, thus preventing the release of 8-OG 106. Since OGG1 104 is inhibited, the OGR1 102 probe will remain intact, and the fluorescence emission from tCo will be quenched by 8-OG. Although FIG. 1 illustrates the inhibitor 108 interacting directly with OGG1 104, this should not be taken to limit these embodiments to any particular type of inhibition, as such OGG1 inhibition could be accomplished through competitive inhibition, noncompetitive inhibition, uncompetitive inhibition, and/or any other type of inhibition. Conventional assays do not allow for accurate measurement of the excision activity by OGG1.

In various embodiments, the fluorogenic assay may be used in high throughput to identify small-molecule OGG1 inhibitors. Utilizing the assay, structure-activity relationships of a broad set of derivatives as potential inhibitors of the enzyme may be determined, as described in greater detail herein.

Identification of OGG1 Inhibitors

Figure 2A:
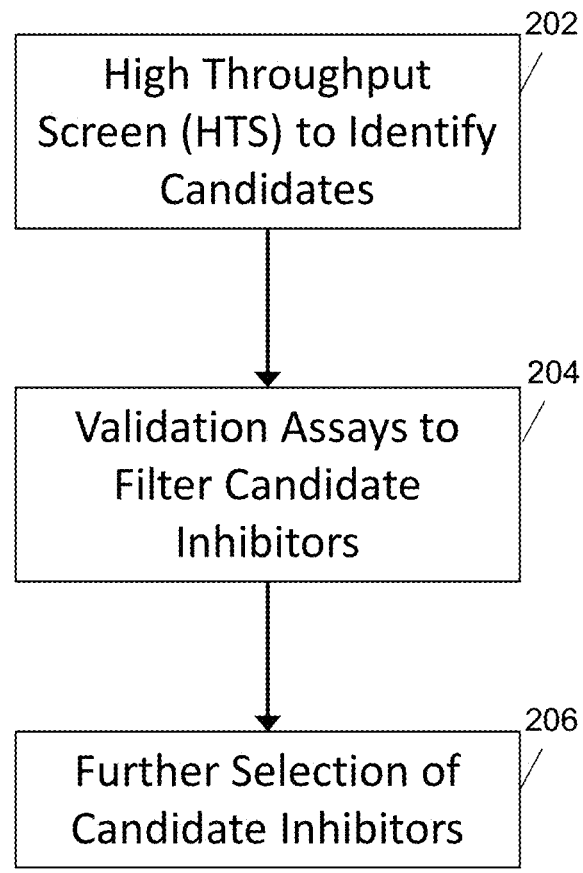

To identify OGG1 inhibitors, it can be necessary to screen numerous compounds. An embodiment of the screening and identification process is illustrated in FIG. 2A. As shown here, some embodiments use a high-throughput screen (HTS) 202 of many compounds to identify candidate compounds for the inhibition of OGG1. The HTS can utilize an assay such as described above and in FIG. 1. In some embodiments, the HTS step uses a single assay of each compound at a single concentration to identify candidates that inhibit OGG1. The single concentration can be performed at concentrations of 0.1 µM, 0.2 µM, 0.1 µM, 1 µM, 2 µM, 5 µM, 10 µM, 20 µM, 50 µM, 100 µM, 200 µM, 500 µM, 1000 µM, or 2000 µM. Upon identifying candidate inhibitors, some embodiments will validate 204 these inhibitors by performing additional assays of the OGG1 inhibition. The validation step can be accomplished a number of ways, including performing an OGR1 assay over a number of concentrations of the compound. In some embodiments, candidates are validated by titration over a 4-fold, 6-fold, 8-fold, 10-fold, 12-fold, or 20-fold concentration range. Additional embodiments will further select for candidate inhibitors 206. Further selection can take various forms, including cost of production or acquisition, ease of manufacture, and/or ease of manipulation of the compound. Upon the further selection, a single candidate may be available for use as an OGG1 inhibitor.

An exemplary methodology for identifying OGG1 inhibitors using embodiments of the fluorogenic assay is provided in FIG. 2B. As shown in this exemplary embodiment, the analysis was begun with an HTS of the PubChem-annotated library compounds using recombinant human OGG1 (hOGG1) enzyme and the OGR1 probe assay. Approximately 26,000 compounds were chosen for initial screening, and the assay was carried out at a single 20 µM concentration. In the exemplary embodiment, the HTS screen 202' led to over 300 initial hit compounds with varied chemical structures. After the HTS, candidate inhibitors were validated 204'. These candidate structures were validated by titration over an 8-fold concentration range. The validation assay in the exemplary embodiment yielded several validated inhibitor compounds 206', including, embodiments of a tetrahydroquinoline sulfonamide derivative inhibitor 208' with significant inhibitory activity, which will be described in greater detail below. The assay according to embodiments was also used to determine structure-activity relationships of a broad set of derivatives as potential inhibitors of the enzyme.

Embodiments of OGG1 Inhibitors

Many embodiments are directed to highly potent, selective and stable small molecule inhibitors of OGG1. Many such embodiments are directed to tetrahydroquinoline sulfonamide derivatives having a general formula (1), below:

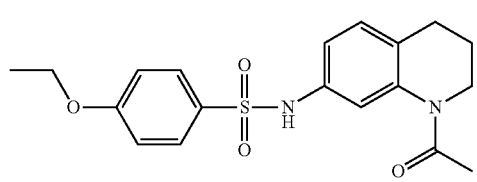

1

Figure 3:
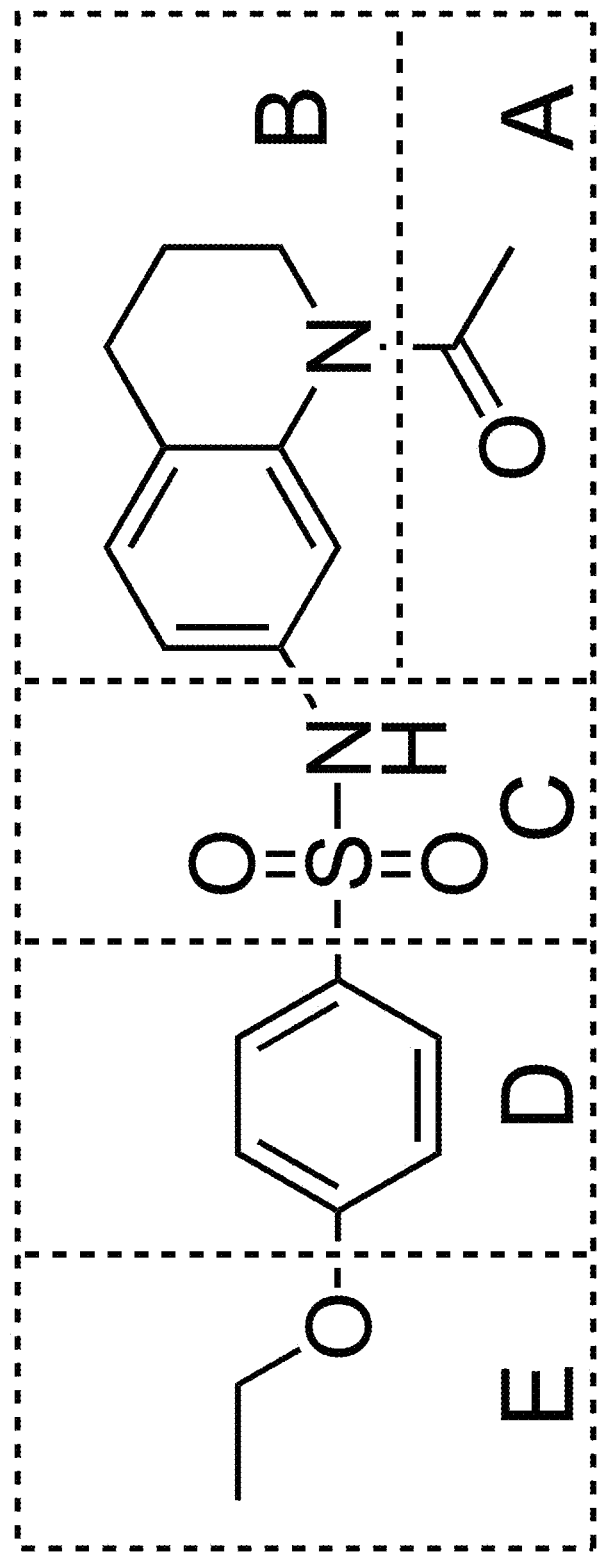
FIG. 3 provides a diagram of an OGG1 inhibitor according to embodiments.
Figure 4A:
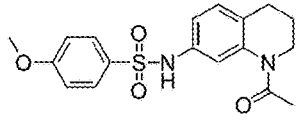
Figure 4A:
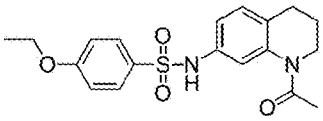
Figure 4A:
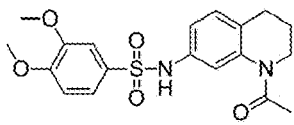
Figure 4A:
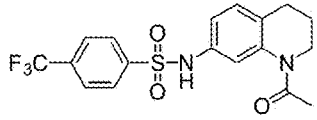
Figure 4A:
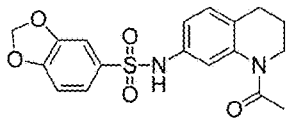
Figure 4A:
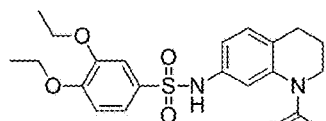
Figure 4A:
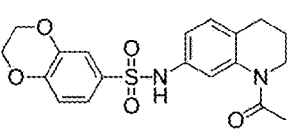
Figure 4D:
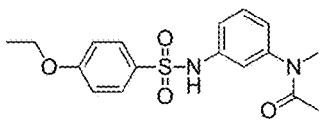
Figure 4D:
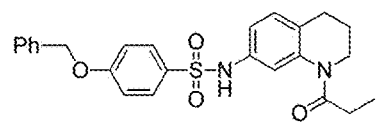
Figure 4D:
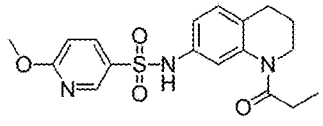
Figure 4D:
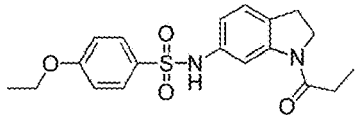
Figure 4D:
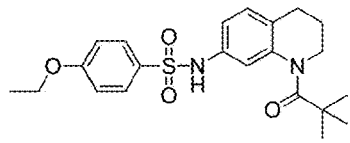
Figure 4D:
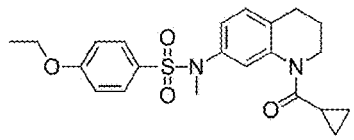
Figure 4D:
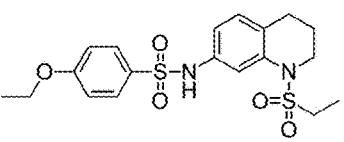
Figure 4F:
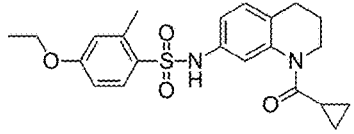
Figure 4F:
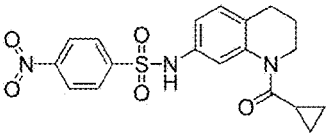
Figure 4F:
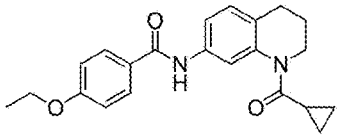
Figure 4F:
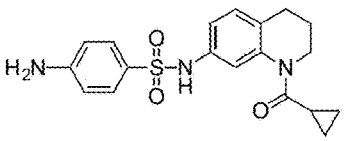
Figure 4F:
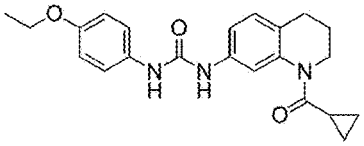
Figure 4F:
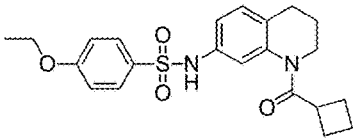
Figure 4F:
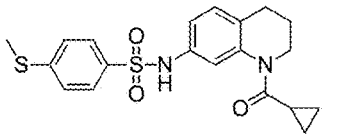
Figure 4H:
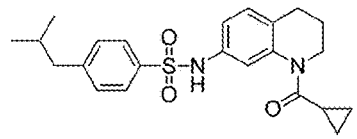
Figure 4H:
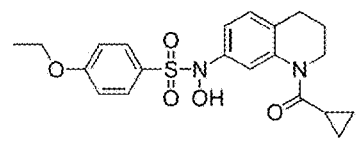
Figure 4H:
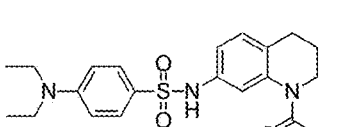
Figure 4H:
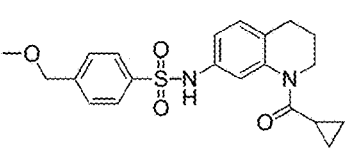
Figure 4H:
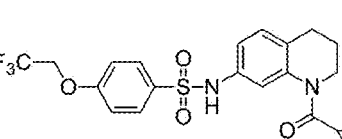
Figure 4H:
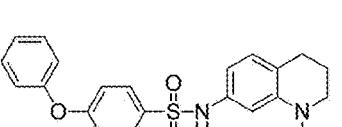
Figure 4H:
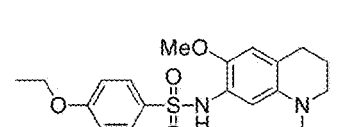
Figure 4J:
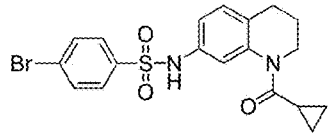
Figure 4J:
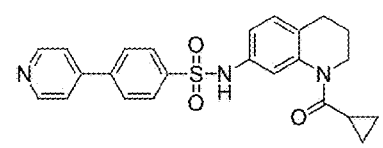
Figure 4J:
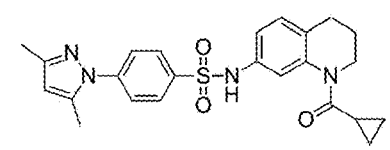
Figure 4J:
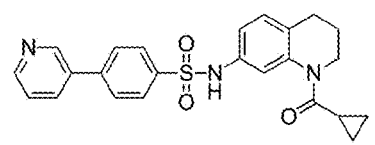
Figure 4J:
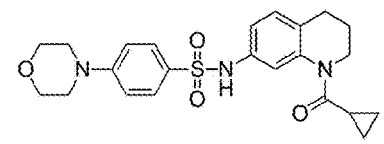
Figure 4J:
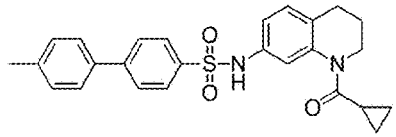
Figure 4J:
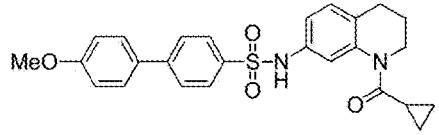
Figure 4K:
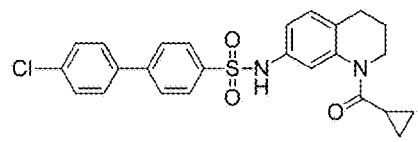
Figure 4K:
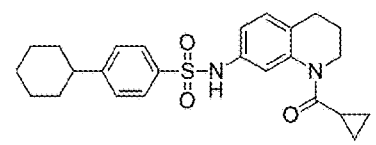
Figure 4K:
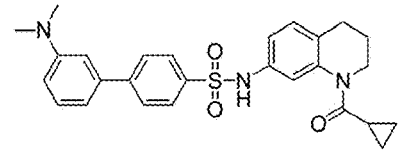
Figure 4K:
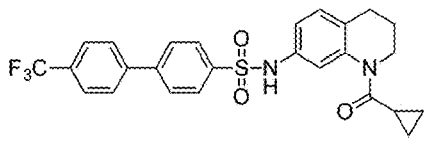
Figure 4K:
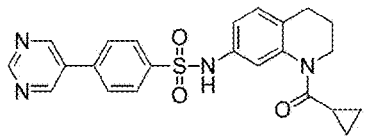
Figure 4K:
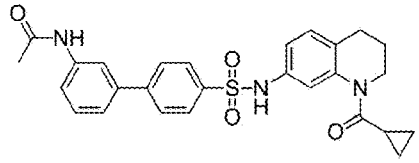
Figure 4K:
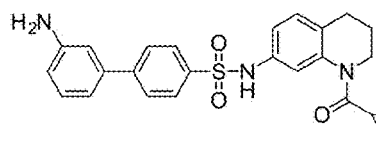

In many embodiments, derivatives of the base tetrahydroquinoline sulfonamide scaffold (1) may be divided into five fragments A to E, as depicted in FIG. 3 that may be modified to form many different active derivatives. As shown, Fragment B consists of a core tetrahydroquinoline structure, and A is a substituent on the nitrogen atom of this core structure. Fragment C, a sulfonamide, is a linker between core structure B and Fragment D, a benzene ring. Fragment E is a substituent of this aromatic ring. By varying these fragments it is possible to develop a systematic understanding of how each fragment influences OGG1 base excision of embodiments of OGG1 inhibitors as measured by the OGR1 assay.

Variation of Fragment A

In many embodiments of inhibitors, Fragment A was varied by providing alternative substituents ($R^1$) on the nitrogen atom of the base tetrahydroquinoline inhibitor according to:

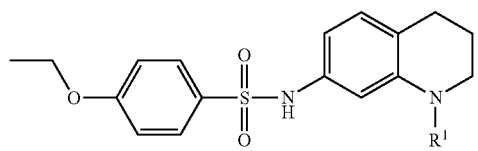

Assays of these compounds were carried out over a three-log concentration range to differentiate weak inhibitors from stronger ones. A summary of these results is provided in Table 1, below. As summarized, embodiments of inhibitor (1) (with acetamide substituent as $R^1$) showed significant inhibition of OGG1 at 20 μM and approximately 50% inhibition at 2 μM. Homologation of acetamide to ethylamide (2) had little effect on inhibition. Embodiments having larger substituents (3-6) still showed activity, but at a lower level. However, cyclopropylamide analog 7 showed significantly more potent inhibition activity, and was also more active than the closely related isopropyl variant 5. A slightly larger ring (cyclobutyl compound 8) showed somewhat lower potency. Other $R_1$ substituents were also attempted, including varying the carbonyl itself. Sulfonamide analog 9, urea analog 10 and reduced analog 11 were prepared and assayed. However, these compounds showed little or no inhibition even at 20 μM.

TABLE 1

| Cmpd | $R^1$ | Enzyme activity, % of control at 20 μM[a] | 2 μM[a,b] | 200 nM[a,b] |
|---|---|---|---|---|
| 1 | | 4.7 ± 3.0 | 47 ± 3.5 | 74 |
| 2 | | 3.7 ± 0.83 | 51 ± 1.4 | n.t. |
| 3 | | 79 | ≥100 | n.t. |
| 4 | | 51 | 93 | n.t. |
| 5 | | 52 | 96 | n.t. |
| 6 | | ≥100 | n.t. | n.t. |
| 7 | | 5.8 ± 1.9 | 41 ± 1.7 | 82 ± 12 |
| 8 | | 33 | 69 | n.t. |
| 9 | | 92 | 96 | n.t. |
| 10 | | 77 | 87 | n.t. |
| 11 | | 83 | ≥100 | n.t. |

[a] % of control values are ratio of enzyme activity to control (no compound) based on slopes of initial rate (first 12 min of assay).
[b] n.t., not tested.

Accordingly, in many embodiments, a substituted or unsubstituted carbonyl group is maintained on the tetrahydroquinoline nitrogen atom for activity. Although substituents at Fragment A may vary, in many embodiments the substituents are confined to smaller substituted or unsubstituted chain or ringed moieties (e.g., $C_4$ or less). In other embodiments, chained moiety substituents of Fragment A are constrained to $C_2$ or less, including for example, acetamide and ethylamide. In still other embodiments ringed moiety substituents of Fragment A are constrained to $C_3$, including, for example, cyclopropylamide group.

Although specific embodiments are provided above, it will be understood that in view of the considerations listed for Fragment A, in many embodiments, $R^1$ may be selected from the list consisting of:

hydrogen, deuterium;

Group 1: saturated or unsaturated, linear, branched, or cyclic hydrocarbon (referred to, herein, as "alkyl"), cycloalkylalkyl, aryl, arylalkyl (including benzyl), which may consist of at least a 1-4 carbon atoms, each of which may be further optionally substituted, and any combination thereof;

Group 2: all of the entities of Group 1, wherein one or more carbon atoms (except for the attachment point carbon atom) is replaced by one of: O, S, N, Si, P, B, or any combination thereof; of which N, P or B may further have one or more —H, —OH, —OR, or —R substitutions, wherein, in turn, every R is, independently, any one entity of the Group 1;

Group 3: all of the entities of Groups 1 and 2, wherein one or more hydrogen atoms are substituted with one of functionalities from the list: —OR, —NR₂, —ONO₂, —CN, —N₃, —NO₂, —SR, —5O2R, —SO₃R, —SCN, —NCS, —OP(O)(OR)₂, —B(OR)₂; wherein every R is, independently, one of: H or any entity from Group 1;

Group 4: all of the entities of Groups 1, 2, and 3, wherein one or more (and up to all available) hydrogen atoms are replaced with a halogen atom or deuterium atom;

Group 5: —C(O)R¹⁰, wherein R¹⁰ is any entity from Groups 1, 2, 3 and 4;

Group 6: —C(O)N(H)R¹¹, wherein R¹¹ is any entity from Groups 1, 2, 3, and 4;

Group 7: —C(O)N(R¹²)R¹³, wherein R¹² and R¹³ are each, independently, any entity from Groups 1, 2, 3 and 4; and Group 8: —S(O)₂R¹⁴, wherein R¹⁴ is any entity from Groups 1, 2, 3, and 4.

Variation of Fragment B

In other embodiments, Fragment B, the tetrahydroquinoline core structure of the inhibitor (1) was varied by providing alternative base structures R² according to formula:

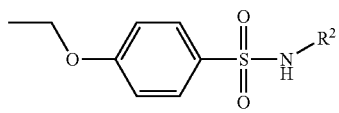

Assays of these compounds were carried out over a three-log concentration range to differentiate weak inhibitors from stronger ones. A summary of these results is provided in Table 2, below. As summarized, single aromatic ring compound 12 and reduced size (to 5-membered) amine ring dihydroindole 13 showed low activity. The expanded (to 7-membered) amine ring analog 14 was also examined, but displayed lower inhibition activity than the 6-membered amine ring analog 7 shown in Table 1. To test the effects of the carbon skeleton of the tetrahydropyridine ring, an oxygen atom (15) was introduced, but this showed lower inhibition, suggesting a relatively hydrophobic contact with the enzyme at this position. A methoxy substituent was installed on the benzene ring of the tetrahydroquinoline skeleton (16), but this almost completely abrogated inhibitory activity. Finally, the cyclopropylamide substituent was repositioned by one atom in the tetrahydroisoquinoline derivative 17, but this also greatly lowered activity.

TABLE 2

| Cmpd | R² | Enzyme activity, % of control at 20 μM[a] | 2 μM[a,b] | 200 nM[a,b] |
|---|---|---|---|---|
| 12 | | 70 | 96 | n.t. |
| 13 | | ≥100 | 95 | n.t. |
| 14 | | 35 | 76 | n.t. |
| 15 | | 41 | 90 | n.t. |

TABLE 2-continued

| Cmpd | R² | Enzyme activity, % of control at 20 μM[a] | 2 μM[a,b] | 200 nM[a,b] |
|---|---|---|---|---|
| 16 | 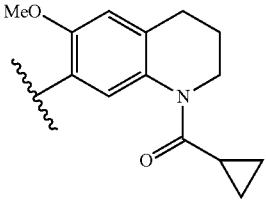 [SMILES: *c1cc2c(cc1OC)CCCN2C(=O)C1CC1] | 93 | ≥100 | n.t. |
| 17 | 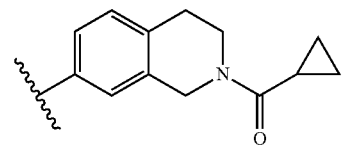 [SMILES: *c1ccc2c(c1)CN(C(=O)C1CC1)CC2] | 88 | 94 | n.t. |

[a] % of control values are ratio of enzyme activity to control (no compound) based on slopes of initial rate (first 12 min of assay).
[b] n.t., not tested.

Accordingly, in many embodiments, the inhibitor incorporates a tetrahydroquinoline skeleton, which has been shown to be quite important to the inhibitory activity of active compounds 1 and 7 (Table 1). In various embodiments, the tetrahydroquinoline is open-ringed, while other embodiments, the tetrahydroquinoline is closed-ringed.

Although specific embodiments are provided above, it will be understood that in view of the considerations listed for Fragment B, in some embodiments, the tetrahydroquinoline skeleton is a tetrahydroquinoline analog, wherein, for example, the benzene ring is replaced with a 5-membered aromatic ring. It will also be understood that the tetrahydroquinoline analogs suitable for Fragment B may include any bicyclic structure, wherein the rings are any combination of 5- or 6-membered saturated, unsaturated, or aromatic cyclic hydrocarbons, and wherein any one or more of the two rings' carbons are replaced with a heteroatom chosen from the list: O, S, N, Si, P, B, or any combination thereof. Furthermore, it will be understood that tetrahydroquinoline analogs for the skeleton of R² include any analog wherein one or more hydrogen atoms around the tetrahydroquinoline (or analog) skeleton may be substituted with deuterium, halogen, alkyl, hydroxyl, amino, alkoxy/alkylamine, —OCN, —NCO, —ONO₂, —CN, —NC, N₃, —NO₂, —SR, —SO₂R, —SO₃R, —SCN, —NCS, —OP(O)(OR)₂, —B(OR)₂; wherein every R is, independently, one of: H or a hydrocarbon, in any combination.

Variation of Fragment C

In other embodiments, Fragment C, the sulfonamide linker between the tetrahydroquinoline and the aromatic substituent was varied by providing alternative base structures R³ according to formula:

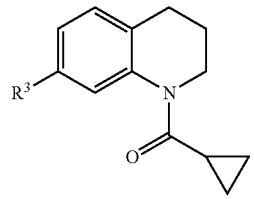

Assays of these compounds were carried out over a three-log concentration range to differentiate weak inhibitors from stronger ones. A summary of these results is provided in Table 3, below. As summarized, diverse linkers were tested in compounds 18-21. N-hydroxy and N-methyl substituted sulfonamides (18 and 19, respectively) were tested, and showed activity, although lower inhibition activity than unsubstituted sulfonamide 7 (Table 1). This suggests possible polar interactions in the enzyme with the N—H group. Amide and urea analogs (20 and 21) were synthesized and assayed, but showed almost no activity.

TABLE 3

| Cmpd | R³ | Enzyme activity, % of control at 20 μM[a] | 2 μm[a,b] | 200 nM[a,b] |
|---|---|---|---|---|
| 18 | 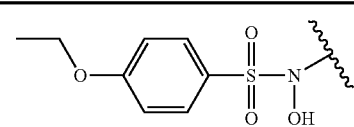 | 21 | 79 | ≥100 |
| 19 | 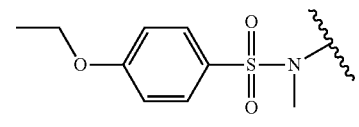 | 79 | 84 | n.t. |

TABLE 3-continued

| Cmpd | R³ | Enzyme activity, % of control at 20 μM[a] | 2 μm[a,b] | 200 nM[a,b] |
|---|---|---|---|---|
| 20 | (4-ethoxybenzamide structure) | ≥100 | ≥100 | n.t. |
| 21 | (4-ethoxyphenyl urea structure) | ≥100 | ≥100 | n.t. |

[a]% of control values are ratio of enzyme activity to control (no compound) based on slopes of initial rate (first 12 min of assay).
[b]n.t., not tested.

Accordingly, in many embodiments, the inhibitor incorporates a sulfonamide functionality with a simple N-X substitution serving as the linker between Fragments D and B. In many such embodiments, X is one of, for example: H, deuterium, hydroxyl (—OH), any regioisomer of saturated or unsaturated $C_{1-3}$-alkyl. In still other embodiments Fragment C is a sulfonamide. In yet many other embodiments, the linker is an iminosulfonamide, of the type —S(O)(NR)N(X)—, or phosphonamide, of the type P(O)(OR)N(X)—, wherein R is, for example, H or a hydrocarbon, and wherein X is, for example, H, deuterium, hydroxyl (—OH), any regioisomer of saturated or unsaturated $C_{1-3}$-alkyl.

Variations of Fragments D and E

In other embodiments, Fragments D and E of inhibitor (1) were varied by providing alternative base structures $R^4$ according to formula:

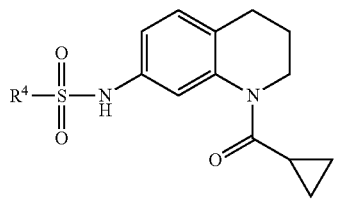

Assays of these compounds were carried out over a three-log concentration range to differentiate weak inhibitors from stronger ones. A summary of these results is provided in Table 4, below. As summarized, an ethyl sulfonamide derivative 22 proved to be quite poorly active, suggesting the importance of the aromatic framework. Accordingly, in many embodiments of inhibitors at least Fragment D comprises an aromatic moiety such as, for example, a benzene.

Subsequently, substituents for Fragment E on the benzene ring of Fragment D were prepared and assayed with OGG1 and the OGR1 probe. Compound 23, carrying a 4-propylphenyl substituent, showed inhibition activity nearly the same as that of compound 7 (Table 1) possessing 4-ethoxyphenyl group. Compound 24 which extends the alkyl chain compared with compound 7 (Table 1) was tested, and also showed activity. The analogs possessing nitrogen and sulfur atoms on the benzene ring were tested and showed some activity, although the heteroatoms had slightly deleterious effects on activity (25 and 26). Accordingly, in other embodiments Fragment D may comprise an aromatic ring (e.g., a benzene ring) having a heteroatom moiety attached thereto, such as, for example, O, N and/or S, attached thereto. The disubstituted compound 27 also showed activity, although with slightly lower inhibition than mono-substituted compound 7 (Table 1). Accordingly, in various embodiments Fragment D may incorporate multiple substitutions about the aromatic ring thereof. Testing of compound 28 which has a diphenyl ether group, showed almost the same activity as compound 7 (Table 1) with its ethoxy group. Therefore, the dibenzofuranyl analog 29 and biphenyl analog 30 was designed and synthesized as rigidified variants of the diphenyl ether compound. The resultant compound 29 showed low activity, but compound 30 had more potent activity than either diphenyl ether 28 and ethoxyphenyl compound 7 (Table 1). Cyclohexylphenyl derivative 31 showed almost the same activity as biphenyl derivative 30, but a more polar morpholinophenyl substituent (32) had a poor effect on the activity. Pyrazolylphenyl and pyridylphenyl analogs (33 and 34) containing a polar nitrogen atom were also subjected to the assay. It was found that compound 34 gave slightly stronger inhibitory activity than biphenyl compound 30, displaying ca. 40% inhibition of activity at 200 nM. Accordingly, in many embodiments Fragments D and E comprise a single linked multi-ring structure, incorporating, for example, diphenyl, diphenyl ether, cyclohexylphenyl, or multi-ring structure containing a polar nitrogen atom, such as, for example, pyrazolylphenyl or pyridylphenyl.

TABLE 4

| Cmpd | R⁴ | Enzyme activity, % of control at 20 μM[a] | 2 μM[a,b] | 200 nM[a,b] |
|---|---|---|---|---|
| 22[c] | (ethyl) | 74 | 94 | n.t. |
| 23 | (4-propylphenyl) | 14 | 35 | 74 |

TABLE 4-continued

| Cmpd | R⁴ | Enzyme activity, % of control at 20 μM[a] | 2 μM[a,b] | 200 nM[a,b] |
|---|---|---|---|---|
| 24 | (propoxy-phenyl) | n.t. | 19 | 95 |
| 25 | (ethylamino-phenyl) | 10 | 58 | ≥100 |
| 26 | (methylthio-phenyl) | 3.6 | 53 | 75 |
| 27 | (ethoxy-methylphenyl) | 22 | 71 | n.t. |
| 28 | (phenoxy-phenyl) | 8.3 | 41 ± 2.0 | ≥100 |
| 29 | (dibenzofuranyl) | 71 | 82 | n.t. |
| 30 | (biphenyl) | n.t. | 29 ± 7.0 | 90 ± 6.2 |
| 31 | (cyclohexyl-phenyl) | n.t. | 25 | 87 |
| 32 | (morpholino-phenyl) | n.t. | 76 | 84 |
| 33 | (pyrazolyl-phenyl) | 14 ± 3.2 | 45 ± 1.3 | 81 |
| 34 | (pyridyl-phenyl) | 2.0 | 23 ± 1.5 | 61 ± 1.3 |

[a]% of control values are ratio of enzyme activity to control (no compound) based on slopes of initial rate (first 12 min of assay).
[b]n.t., not tested.
[c]Acyl group of nitrogen atom on tetrahydroquinoline skeleton is propionyl group.

In view of such considerations for Fragment D, in many embodiments, R⁴ group is one of:
  a mono-, bi-, tri-, or more-cyclic aryl or heteroaryl, wherein at least one ring is an aromatic ring of up to $C_6$ size and substitution, and
  the other rings, if any, are saturated, unsaturated, or aromatic hydrocarbons or heteroatomic hydrocarbons of any size and substitution, and wherein
  the said rings are either connected, including via 1 or more atom-long linkers, or fused; and wherein
  a heteroatom is optionally present in any one or more positions of the R⁴ group, including as a member of any of the rings, or ring linkers, or ring functionalities, and is selected from the group: O, S, N, Si, P, B; and wherein
  any one or more position within R⁴ group, wherein available carbon or heteroatom, is further optionally and independently functionalized with any one or more moieties selected from the list:
  saturated or unsaturated, linear or branched alkyl or haloalkyl, or any combination thereof,
  halogen, deuterium, —OR, —SR, —NR₂, —OCN, —NCO, —ONO₂, —CN, —NC, —N₃, —NO₂, —SO₂R, —SO₃R, —SCN, —NCS, —OP(O)(OR)₂, —B(OR)₂, —C(=O)R, —C(=O)OR, —OC(=O)R, —C(=O)NR₂, —OC(=O)NR₂, —NRC(=O)R, —NRC(=O)OR, —NRC(=O)NR₂, —NRS(=O)₂R, —NRS(=O)₂NR₂, —S(=O)R, —S(=O)₂R, and —S(=O)₂NR₂,
  wherein every R is, independently, one of: H or, saturated, unsaturated or halogenated to any extent hydrocarbon or heteroatom hydrocarbon, and
  independent R groups can optionally be joined to form additional rings.

Variations of Fragment E

In other embodiments, Fragment E of inhibitor (1) was varied by providing alternative base structures R⁵ assuming a Fragment D incorporating an aromatic ring according to formula:

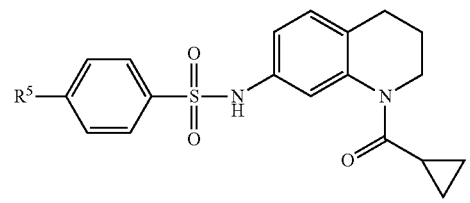

Assays of these compounds were carried out over a three-log concentration range to differentiate weak inhibitors from stronger ones. A summary of these results is provided in Table 5, below. As summarized, the structural effects of substituents on the terminal aromatic ring of embodiments of inhibitor 30 were investigated by synthesizing compounds 35-39 (Table 5). When 4-trifluoromethyl as an electron withdrawing group and 4-methoxy as an electron donating group were compared (35 and 36), the more polar and electron-donating group (4-methoxy) assisted the activity more than the electron-withdrawing group. Moving this substituent's position, the 3-methoxy compound 37 resulted in more potent activity than the 4-substituted compound 36. Therefore, varied substituents at the meta-position of this benzene ring were examined. Compound 38 (with a dimethylamino group) and compound 39 (possessing an acetylamino group) were synthesized and assayed. The compound 38 showed similar activity as methoxy compound 37, but the acetamide 39 showed higher activity than either of these, with inhibition activity of about 50% at 200 nM. When compounds 40 and 41 which have reverse amide structure, were investigated these compounds showed yet higher activity, and compound 41 (SU0268), possessing a meta-carboxamide group, had the strongest inhibitory activity of all compounds in the study.

TABLE 5

| Cmpd | $R^5$ | Enzyme activity, % of control at 20 μM$^a$ | 2 μM$^{a,b}$ | 200 nM$^{a,b}$ |
|---|---|---|---|---|
| 35 | F$_3$C-⌬- | n.t. | 72 | 97 |
| 36 | MeO-⌬- | n.t. | 31 | 79 |
| 37 | MeO-⌬- (meta) | n.t. | 13 | 67 |
| 38 | Me$_2$N-⌬- (meta) | n.t. | n.t. | 70 |
| 39 | AcNH-⌬- (meta) | n.t. | 12 ± 2.0 | 53 ± 4.9 |
| 40 | HN(Me)C(O)-⌬- (meta) | n.t. | n.t. | 48 |

TABLE 5-continued

| Cmpd | $R^5$ | Enzyme activity, % of control at 20 μM$^a$ | 2 μM$^{a,b}$ | 200 nM$^{a,b}$ |
|---|---|---|---|---|
| 41 | H$_2$N-C(O)-⌬- (meta) | n.t. | 4.8 | 39 ± 2.5 |

$^a$% of control values are ratio of enzyme activity to control (no compound) based on slopes of initial rate (first 12 min of assay).
$^b$n.t., not tested.

Accordingly, in many embodiments, the inhibitor incorporates a polar and electron-donating group, such as, for example, a methoxy, dimethylamino, acetylamino, carboxamino, etc. at Fragment E. In various other embodiments, Fragment E is disposed at either position 3 or 4 on the aromatic ring of Fragment D. In some such embodiments, Fragment E comprises a meta-carboxamide group.

In many embodiments, Fragment E ($R^5$) further optionally comprises any one of:
hydrogen, deuterium;
saturated or unsaturated, linear or branched alkyl or haloalkyl, or any combination thereof;
halogen, —OR, —SR, —NR$_2$, —OCN, —NCO, —ONO$_2$, —CN, —NC, —N$_3$, —NO$_2$, —SO$_2$R, —SO$_3$R, —SCN, —NCS, —OP(O)(OR)$_2$, —B(OR)$_2$, —C(═O)R, —C(═O)OR, —OC(═O)R, —C(═O)NR$_2$, —OC(═O)NR$_2$, —NRC(═O)R, —NRC(═O)OR, —NRC(═O)NR$_2$, —NRS(═O)$_2$R, —NRS(═O)$_2$NR$_2$, —S(═O)R, —S(═O)$_2$R and —S(═O)$_2$NR$_2$, wherein every R is, independently, one of: H or, saturated, unsaturated or halogenated to any extent hydrocarbon or heteroatom hydrocarbon, and independent R groups can optionally be joined to form additional rings Accordingly, embodiments of inhibitors may comprise a structure wherein Fragment B comprises a tetrahydroquinoline skeleton having a substituent at Fragment A comprising a substituted or unsubstituted chain or ringed moieties (e.g., C$_4$ or less), in some embodiments a chain moiety substituent of C$_2$ or less, including for example, acetamide and ethylamide, in still other embodiments a ringed moiety of C$_3$, including, for example, cyclopropylamide group. In such embodiments, Fragment C comprises a benzenesulfonamide having a simple "N-X" substitution attached thereto. In many such embodiments, the X may include, for example, —H, -hydroxy or -methyl functionality, such as, for example, "N-X" affords benzenesulfonamide as Fragment C. In some such embodiments, Fragment D comprises at least a single or multi-ringed substituted or unsubstituted aromatic moiety. In some such embodiments, the aromatic moieties may possess a heteroatom, such as, for example, O, N and/or S, attached thereto. In other such embodiments, Fragment D may comprise a single linked multi-ring structure, incorporating, for example, diphenyl, diphenyl ether, cyclohexylphenyl, or multi-ring structure containing a polar nitrogen atom, such as, for example, pyrazolylphenyl or pyridylphenyl. Finally, in embodiments Fragment E incorporates a polar and electron-donating group, such as, for example, a methoxy, dimethylamino, acetylamino, carboxamino, etc. disposed at either position 3 or 4 on the terminal aromatic ring of Fragment D. In some such embodiments, Fragment E comprises a meta-carboxamide group. Exemplary embodiments of various derivatives made in accordance with embodiments are provided in FIGS. 4A-4M.

Although certain groups and structures are described above, it will be understood that other embodiments may also be incorporated within the scope of the disclosure. Specifically, the biological activity of small molecules in animals and humans depends in part on their stability, lifetime and concentration in cells, blood and tissue. Stability and lifetime are commonly reduced when a molecule is metabolized rapidly to a different, non-optimal structure. It is well known to those skilled in the art that a common pathway of metabolism of small molecules is the oxidation of C—H bonds on the molecule, resulting in the replacement of hydrogens with hydroxyl and carbonyl groups.

Figure 5:
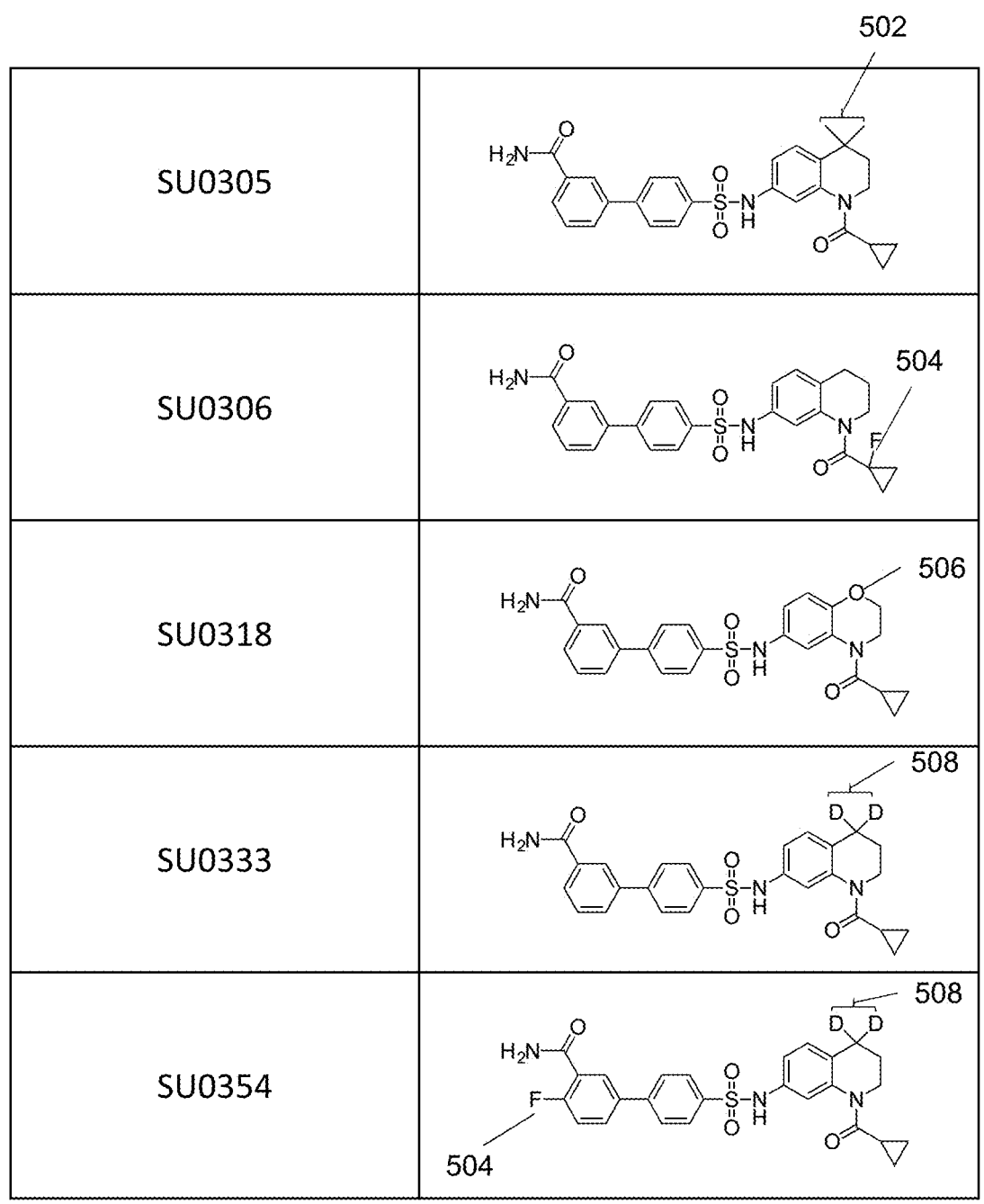
FIG. 5 provides diagrams of OGG1 inhibitors with additional substitutions according to embodiments.

Accordingly, some embodiments incorporate the replacement of hydrogen atoms with deuterium, fluorine and/or methyl groups. Additionally, some embodiments incorporate the replacement of C—H groups with heteroatoms, such as oxygen, sulfur, nitrogen, or another heteroatom. Further, many embodiments will incorporate the replacement of hydrogen atoms and C—H groups. Several exemplary embodiments incorporating replacements shown in FIG. 5. As shown, in these embodiments, multiple positions of the inhibitors are substituted with one or more of methyl groups 502, fluorine 504, oxygen heteroatoms 506, and/or deuterium 508.

Such embodiments in principle have the potential to demonstrate increased lifetime in animal molecules and increase average concentrations in vivo after dosing. This was confirmed by studies of embodiments of such inhibitors conducted in rat microsomes, which showed that some of these modified inhibitors demonstrate increased molecular stability without strongly decreasing inhibitory activity.

Methods of Synthesizing Inhibitors

Figure 6A:
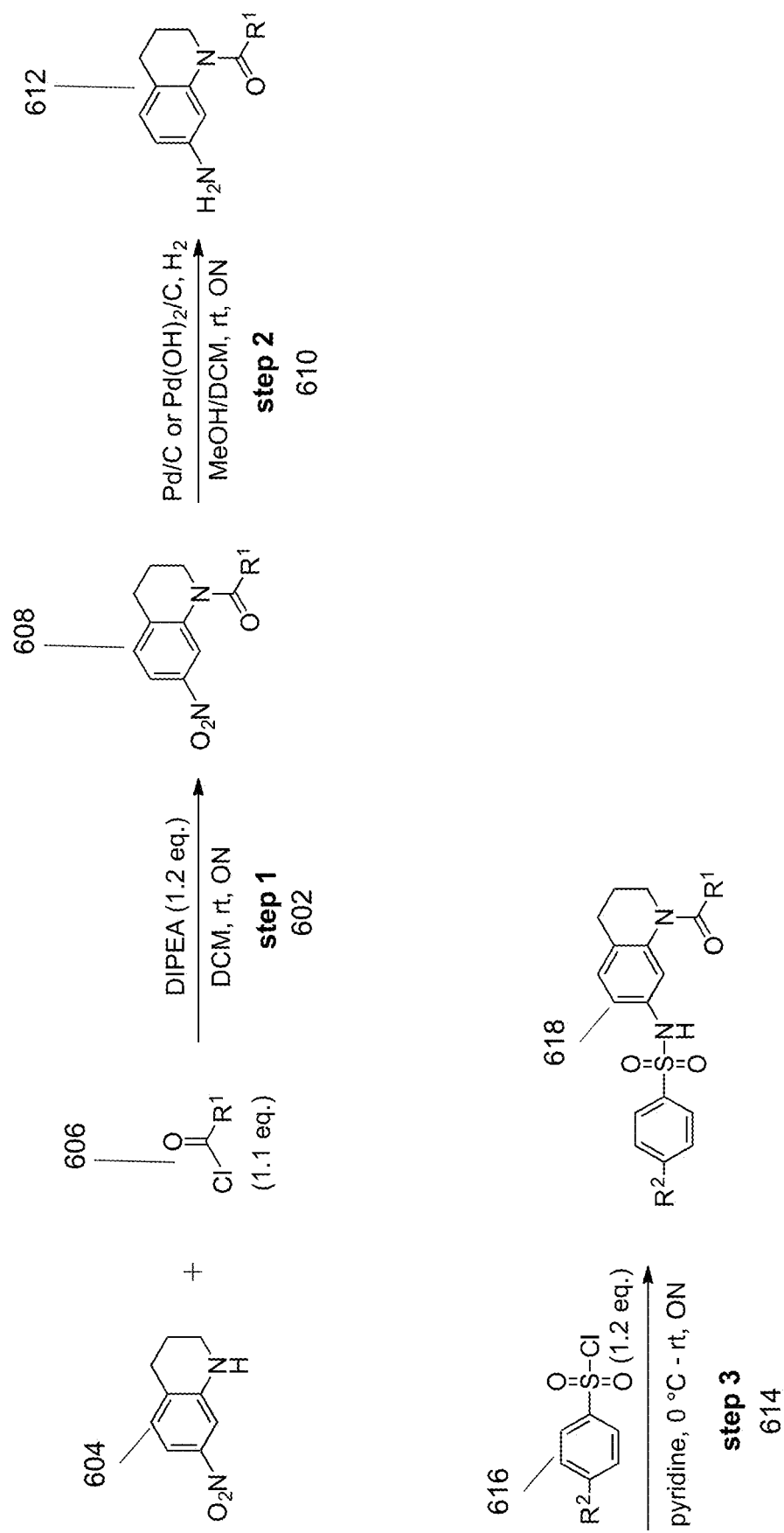
FIGS. 6A and 6B provide schematic diagrams of methods for synthesizing OGG1 inhibitors in according to embodiments.

Many other embodiments are directed to methods of synthesizing inhibitors as described above. A general method is provided in FIG. 6A, and summarized below. In FIG. 6A, Step 1 602 combines 7-Nitro-1,2,3,4-tetrahydroquinoline 604 with an acyl chloride 606. In this reaction, the acyl chloride 606 can be added at molar equivalent concentration of the 7-Nitro-1,2,3,4-tetrahydroquinoline 604, or the acyl chloride 606 can be added with a greater equivalent than the 7-Nitro-1,2,3,4-tetrahydroquinoline 604 to increase the amount of the resulting crude product 608. This excess addition of the acyl chloride 606 can be 1.1 equivalents, 1.2 equivalents, 1.3 equivalents, 1.4 equivalents, 1.5 equivalents, 1.6 equivalents, 1.7 equivalents, 1.8 equivalents, 1.9 equivalents, or 2.0 equivalents of acyl chloride 606 to 7-Nitro-1,2,3,4-tetrahydroquinoline 604. Further, this reaction may be undertaken in an appropriate solution, at an appropriate temperature, and for an appropriate amount of time to increase the reaction efficiency, speed, or output of the crude product 608. In a specific embodiment, 7-Nitro-1,2,3,4-tetrahydroquinoline 604 (892 mg, 5.0 mmol) is dissolved in dichloromethane (DCM), and then the appropriate acyl chloride 606 (5.5 mmol) and N,N-diisopropylethylamine (DIPEA) (1.05 mL, 6.0 mmol) are added dropwise. The reaction mixture is stirred overnight (ON) at room temperature (rt). After completion of the reaction, the solvent is removed under reduced pressure. Ethyl acetate and water are added to the residue, and the mixture is washed with water and brine, and then dried with magnesium sulfate. The solvent is removed under reduced pressure, and the crude product is used next step without further purification. (See, e.g., Sloss, M. K., et al., WO2009089042, the disclosure of which is incorporated herein by reference.)

At Step 2 610 in FIG. 6A, the crude product 608 undergoes a reaction to hydrogenate the nitro group to an amino group. This reaction may be undertaken in an appropriate solution, at an appropriate temperature, and for an appropriate amount of time to increase the reaction efficiency, speed, or output of the product of Step 2 612. As illustrated in FIG. 6A, crude product 608 is dissolved in methanol (MeOH) and DCM and a catalyst of palladium on carbon (Pd/C) or palladium hydroxide on carbon (Pd(OH)$_2$/C) is added in the presence of hydrogen gas (H$_2$). This reaction can occur by many known ways in the art. In a specific embodiment, the crude product of step 1 608 (5.0 mmol) is dissolved in methanol 20 mL and dichloromethane 5 mL, and palladium 10% on carbon (94 mg) is added to the solution. The solution is degassed with argon gas, and then hydrogen gas is introduced. The reaction mixture is stirred overnight at room temperature. After completion of the reaction, the reaction mixture is filtered through celite. The solvent is removed under reduced pressure. The residue is purified by crystallization or silica gel column chromatography to yield the corresponding products.

At Step 3 614 of some embodiments, an appropriate sulfonyl chloride 616 is added to the product of Step 2 612. In this reaction, the sulfonyl chloride 616 can be added at molar equivalent concentration of the product of Step 2 612, or the sulfonyl chloride 616 can be added with a greater equivalent than the product of Step 2 612 to increase the amount of the resulting corresponding product 618. This excess addition of the sulfonyl chloride 616 can be 1.1 equivalents, 1.2 equivalents, 1.3 equivalents, 1.4 equivalents, 1.5 equivalents, 1.6 equivalents, 1.7 equivalents, 1.8 equivalents, 1.9 equivalents, or 2.0 equivalents of sulfonyl chloride 616 to product of Step 2 612. Further, this reaction may be undertaken in an appropriate solution, at an appropriate temperature, and for an appropriate amount of time to increase the reaction efficiency, speed, or output of the corresponding product 618. In a specific embodiment, the product of step 2 612 (0.5 mmol) is dissolved in dry pyridine 3 mL, and then the reaction mixture is cooled with an ice bath. The appropriate sulfonyl chloride 616 (0.6 mmol) is added to the solution, and then the reaction mixture is allowed to warm to room temperature. After completion of the reaction, ethyl acetate is added to the solution. The mixture is washed with 1 M hydrochloric acid and brine, and then dried with magnesium sulfate. The solvent is removed under reduced pressure. The residue is purified by crystallization or silica gel column chromatography to yield the corresponding products. (See, e.g., Rashad, A. A., et al., A. ACS Med. Chem. Lett. 2014, 5, 496-500, the disclosure of which is incorporated herein by reference.)

It should be noted that it may be beneficial to purify certain intermediate compounds produced during the synthesis of the final product 618. As such, one or more chromatography columns or other purification methods may be introduced following each of the steps. Such purification methods can include crystallization, silica gel column chromatography, celite filtration, and/or any other method known in the art.

Figure 6B:
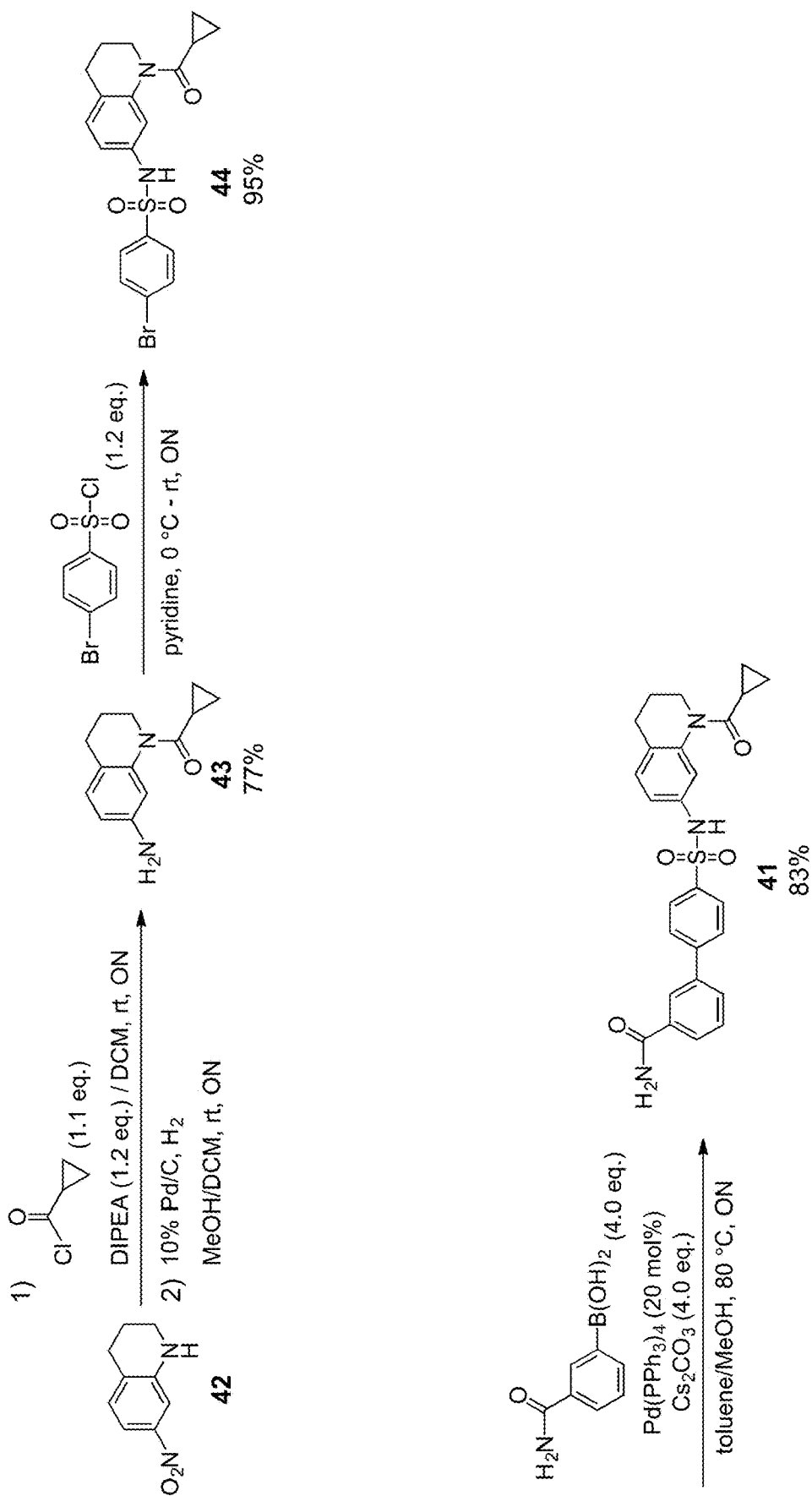

Turning now to FIG. 6B, an exemplary embodiment of the production of an OGG1 inhibitor in accordance with this specification is illustrated and described below.

An exemplary synthetic scheme for producing an OGG1 inhibitor directed specifically at the tetrahydroquinoline biphenyl sulfonamide derivative 41 in accordance with embodiments is depicted in FIG. 6B. As shown, the synthesis commences with the acylation of the commercially available tetrahydroquinoline 42 with cyclopropylcarbonyl chloride in the presence of N,N-diisopropylethylamine (DIPEA). Subsequent 1-atm hydrogenation of the acylated intermediate in the presence of palladium on carbon gave the amine 43 in 77%. (See, e.g., Sloss, M. K., et al., WO2009089042, the disclosure of which is incorporated herein by reference.) Sulfonylation of 44 with 4-bromobenzene sulfonylchloride afforded the sulfonamide 44 in excellent yield. (See, e.g., Rashad, A. A., et al., *ACS. Med. Chem. Lett.* 2014, 5, 496-500, the disclosure of which is incorporated herein by reference.) Construction of the biphenyl structure using Suzuki-Miyaura coupling in the last step with 3-aminocarbonylphenyl boronic acid in the presence of tetrakis(triphenylphosphine)palladium(O) gave the desired 41 in 82%. (See, e.g., Katagiri, K., et al., *Cryst. Growth Des.* 2014, 14, 199-206, the disclosure of which is incorporated herein by reference.) The intermediates 43 and 44 were obtained by crystallization, and this protocol required only one silica column chromatography purification step to isolate 41.

Characterization of Inhibitor Properties

Properties of selected inhibitors are provided below to characterize the performance of exemplary embodiments of the invention. Although some specific inhibitors are discussed, it will be understood that the results are meant only to provide an overview of inhibitor functions and are not meant to be limiting.

$IC_{50}$

Figure 7:
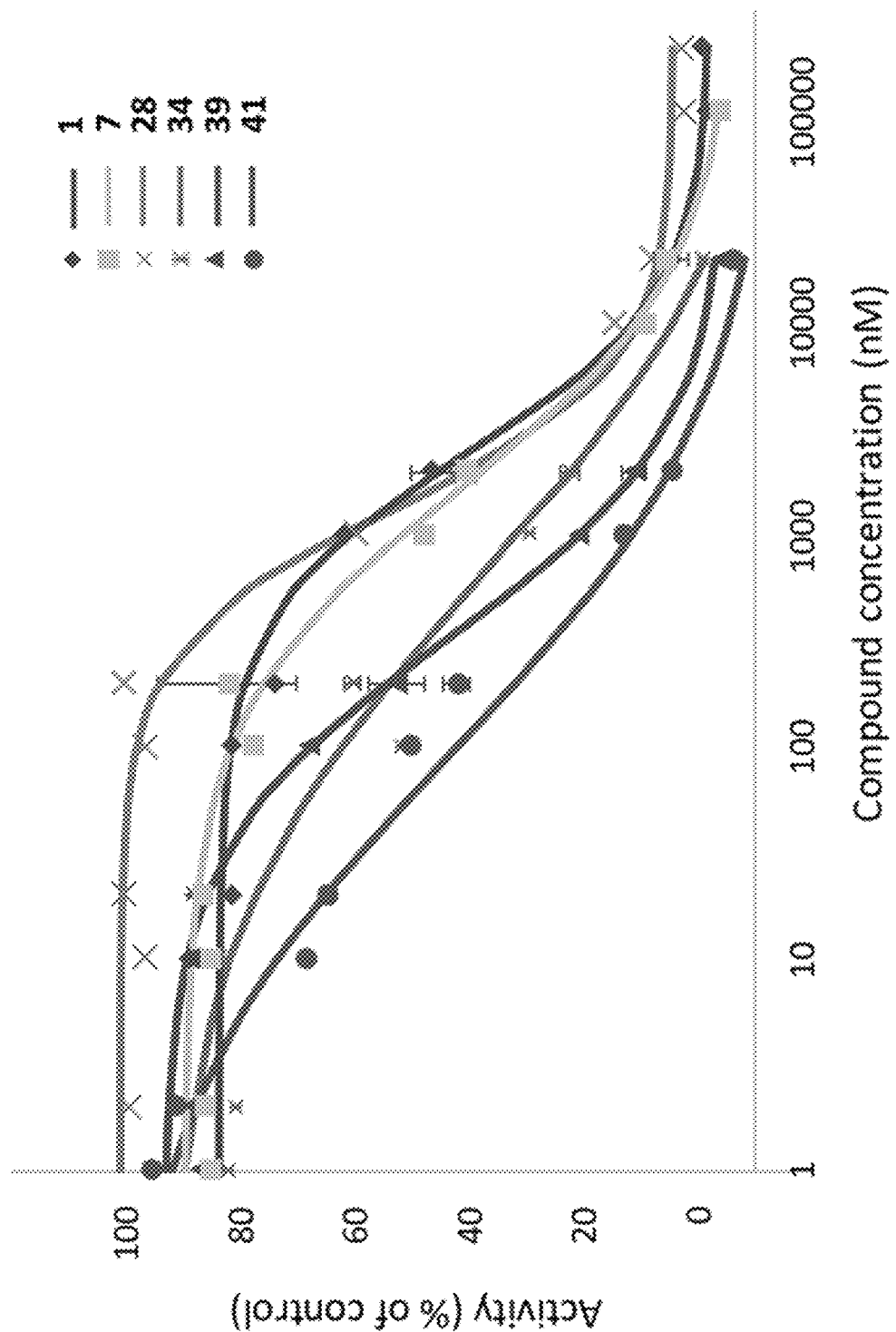
FIG. 7 provides a data plot of titration curves of selected OGG1 inhibitors according to embodiments.

Inhibitors in accordance with some embodiments possess low $IC_{50}$ concentrations. FIG. 7 illustrates titration curves and $IC_{50}$ values for a series of compounds in accordance with some embodiments. In this figure, the degree of OGG1 inhibition was measured relative to a control of uninhibited OGG1. The $IC_{50}$ of compound 1, select key intermediate inhibitors (7 (Table 1), 28 (Table 4), 34 (Table 4), and 39 (Table 5)) and compound 41 (FIG. 6B) were determined using the initial rates method (FIG. 7 and Table 6). The $IC_{50}$ of the hit compound 1 was 1.7 µM. The $IC_{50}$ values of intermediate inhibitors 7 and 28, with modified substituents on tetrahydroquinoline and benzenesulfonamide, were slightly more potent than that of compound 1. The intermediate inhibitors 34 (with pyridine ring) and 39 (with acetylamino group) had considerably higher activity than the lead compound 1, with $IC_{50}$ values below 0.3 µM. The $IC_{50}$ value of the optimized compound 41 was 0.059 µM. ClogP (hydrophobicity) and tPSA (topological polar surface area) was calculated values for the compounds (Table 6) as useful measures of potentially bioactive compounds. (See, e.g., Lipinski, C. A., et al., *Adv. Drug Del. Rev.* 1997, 23, 3-25; and Cox, P. B., et al., *Bioorg. Med. Chem.* 2012, 20, 4564-4573, the disclosures of which are incorporated herein by reference.) The values of ClogP of the compound 7 and 28 were higher than the hit compound 1, but their values of tPSA were almost the same. The potent inhibitors 34, 39 and 41 showed moderate cLogP values (3.4-3.8), and their tPSA values were 79-110, which also fall in the generally accepted range for potential bioactivity.

TABLE 6

$IC_{50}$ of OGG1 inhibitors, and their ClogP and tPSA

| Cmpd | $IC_{50}$ (µM) | ClogP[a] | tPSA[a] |
|---|---|---|---|
| 1 | 1.7 | 2.5 | 76 |
| 7 | 1.1 | 3.6 | 76 |
| 28 | 1.5 | 4.9 | 76 |
| 34 | 0.27 | 3.4 | 79 |

TABLE 6-continued $IC_{50}$ of OGG1 inhibitors, and their ClogP and tPSA

| Cmpd | $IC_{50}$ (µM) | ClogP[a] | tPSA[a] |
|---|---|---|---|
| 39 | 0.25 | 3.8 | 96 |
| 41 | 0.059 | 3.3 | 110 |

[a]see SI for calculation methods.

Surface Plasmon Resonance

Figure 8:
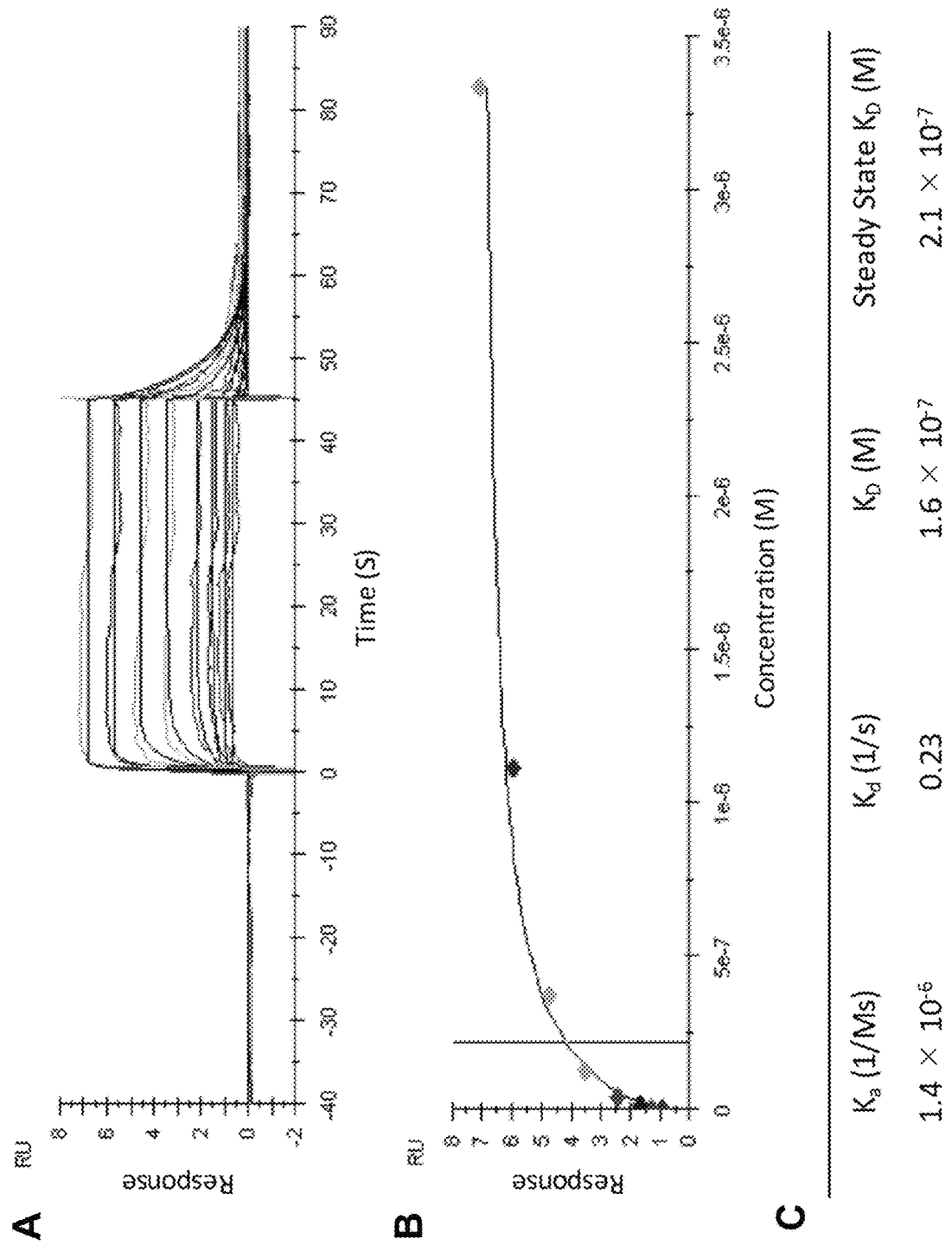
FIGS. 8A-8C provide SPR studies with compound 41, including: 8a) sensorgram plots in kinetic study of OGG1 and inhibitor 41; 8B) plots with concentration (M) on steady state of OGG1 and inhibitor 41; and 8C) $K_a$, $K_d$, $K_D$, and steady state $K_D$, according to embodiments.

Additional embodiments utilize surface plasmon resonance (SPR) to investigate the binding of various compounds to OGG1. FIGS. 8A-8C demonstrate data showing the binding of an inhibitor to OGG1 in accordance with various embodiments. Specifically, FIG. 8A illustrates a sensorgram plot of binding response versus time, while FIG. 8B illustrates binding response versus concentration of an inhibitor. Further, FIG. 8C provides $K_a$, $K_d$ and $K_D$ values that are calculated for compounds of various embodiments. These figures indicate that certain embodiments bind strongly to OGG1.

FIGS. 8A-8C demonstrate SPR studies using compound 41. For this embodiment, the rate of association and affinity are relatively high as compared to the rate of constant, indicating that compound 41 binds strongly to OGG1.

Inhibitor Kinetics

Some embodiments measure Michaelis-Menten parameters of OGG1 with and without the presences of inhibitors in accordance with certain embodiments. In these embodiments, Lineweaver-Burk plots are obtained from Michaelis-Menten curves (FIG. 9), and $K_m$ and $K_{cat}$ values were calculated for various embodiments of OGG1 inhibitors (Table 7). In the embodiment graphed in FIG. 9 and summarized in Table 7, the effect of the inhibitor on OGG1 had little to no effect on $K_m$ and a lowering of $K_{cat}$, which indicates that the illustrated inhibitor is possibly a noncompetitive inhibitor against OGG1. (See, e.g., Mohan, C.; Long, K. D.; Mutneja, M. *An Introduction to Inhibitors and Their Biological Applications*, EMD MILLIPORE, Billerica, 2013, 3-22, the disclosure of which is incorporated herein by reference.)

To investigate the effects of the specific embodiment, SU0268 (compound 41), on inhibition of OGG1, Michaelis-Menten parameters were measured in the absence and presence of this compound at 200 nM and 2 µM concentrations. A Lineweaver-Burk plot was obtained from Michaelis-Menten curves (FIG. 9), and $K_m$ and $K_{cat}$ values were calculated (Table 7). Measuring the effect of the inhibitor showed little or no effect on $K_m$ and a lowering of $k_{cat}$. These results mean that compound 41 has possibilities of competitive inhibition against OGG1. (See, e.g., Mohan, C.; Long, K. D.; Mutneja, M. An *Introduction to Inhibitors and Their Biological Applications*, EMD MILLIPORE, Billerica, 2013, 3-22, the disclosure of which is incorporated herein by reference.)

TABLE 7

$K_m$ and $K_{cat}$ without inhibitor and with inhibitor 41

| | No Inhibitor | 2 µM 41 | 200 nM 41 |
|---|---|---|---|
| $K_m$ (µM) | 1.2 | 1.8 | 8.2 |
| $K_{cat}$ (s$^{-1}$) | 0.046 | 0.040 | 0.057 |
| $K_{cat}/K_m$ (s$^{-1}$µM$^{-1}$) | 0.039 | 0.022 | 0.0070 |

Studies of the Interaction of Inhibitors and Abasic DNA and OGR1 Probe

Figure 10:
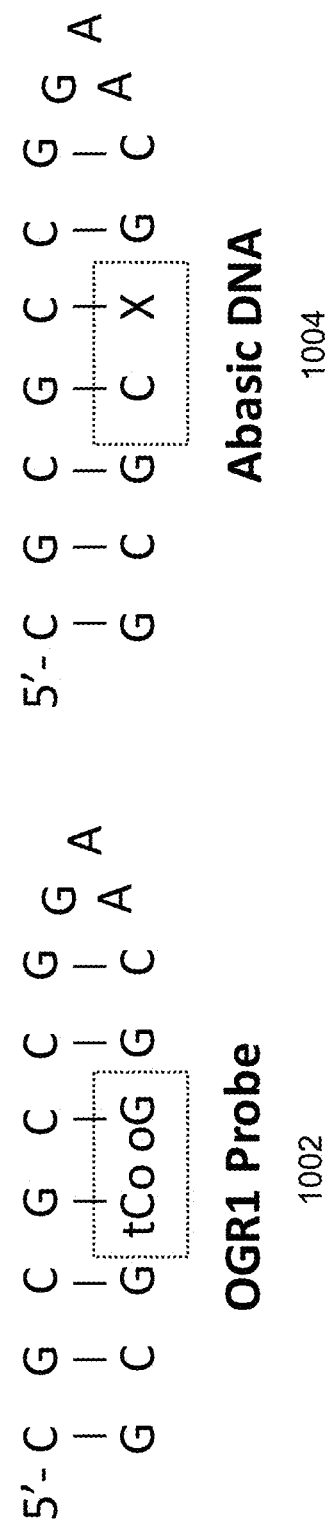
FIG. 10 provides diagrams of the OGR1probe and Abasic DNA according to embodiments.

Additional embodiments measure the interaction of abasic DNA (without 8-OG) and the OGR1 probe with inhibitors of certain embodiments. As illustrated in FIG. 10 (and described above), the OGR1 probe 1002 possesses a tCo next to 8-OG, while the abasic DNA 1004 possesses a normal cytosine (C) next to an abasic site mimic (X). If an inhibitor in accordance with certain embodiments interacts directly with the DNA, melting temperature ($T_m$) of the DNA will change significantly. (See, e.g., Yoshimoto, K.; Nishizawa, S.; Minagawa, M.; Teramae, N. *J. Am. Chem. Soc.* 2003, 125, 8982-8983, the disclosure of which is incorporated herein by reference.) As summarized in Table 8, the almost no change in $T_m$ are demonstrated. Thus, at least some embodiments of OGG1 inhibitors do not interact directly with DNA, suggesting that the inhibitors interact with OGG1 directly.

Table 8 summarizes data from the interaction of abasic DNA (without 8-OG) and OGR1 probe (FIG. 10) (with 8-OG) with the specific embodiment, compound 41. In the both cases of abasic DNA and OGR1 probe, almost no changes of $T_m$ were observed. These results suggest that compound 41 does not bind DNA, and thus interacts with OGG1 specifically rather than its substrate.

TABLE 8

| DNA | $T_{m(-)}/°C.$ | $T_{m(+)}/°C.$ | $\Delta T_m/°C.$ |
|---|---|---|---|
| Abasic DNA[a] | 71.3 ± 0.63 | 71.3 ± 0.29 | 0.0 |
| OGR1 Probe[b] | 82.2 ± 0.77 | 82.5 ± 0.25 | 0.3 |

[a]DNA = 1 µM, [41] = 2 µM (1% DMSO), NEBuffer.
[b][DNA] = 1 µM, [41] = 2 µM (10% DMSO), PBS buffer and betaine (10 mM).[47]

OGG1 Inhibition Selectivity

Figure 11:
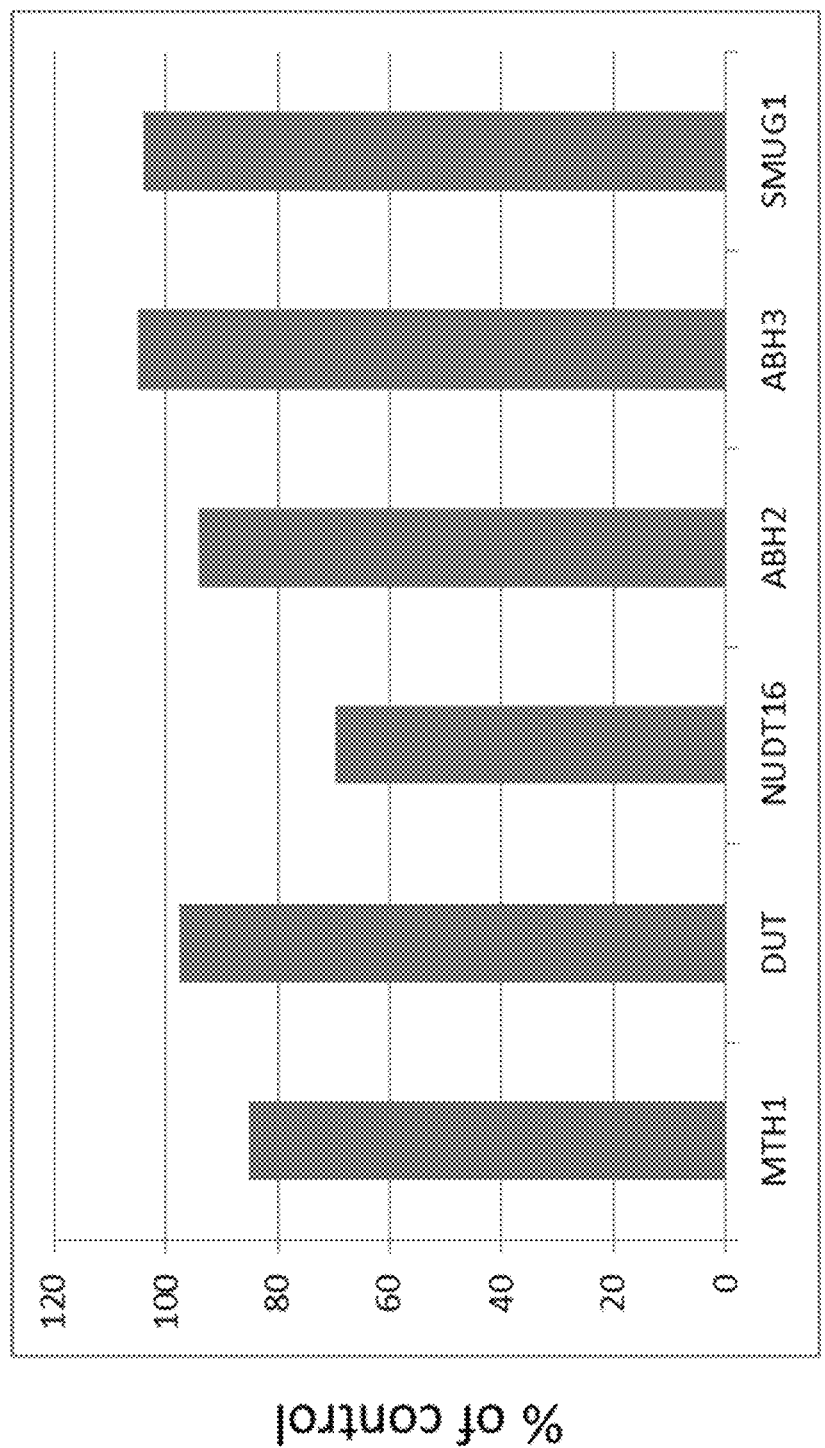
FIG. 11 provides a data plot of the selectivity of an exemplary OGG1 inhibitor tested against varied repair enzymes according to embodiments.

In accordance with some embodiments, the selectivity of various inhibitors in accordance with various embodiments is measured. FIG. 11 illustrates the effect of an inhibitor in accordance with certain embodiments against other repair enzymes that process either 8-oxoguanine nucleotides, bind nucleotides or DNA, or employ base excision mechanisms, including MTH1 (human MutT homolog 1), DUT (deoxyuridine 5'-triphosphate nucleotidohydrolase), NUDT16 (nucleoside diphosphate linked moiety X-type motif 16), ABH2 (alkB homolog 2), ABH3 (Alpha-ketoglutarate-dependent dioxygenase alkB homolog 3), and SMUG1 (Single-strand selective monofunctional uracil DNA glycosylase).). (See, e.g., Carter, M., et al., *Nat. Commun.* 2015, 6, 7871; Cedergren-Zeppezauer, E. S., et al., *Nature* 1992, 355, 740-743; Iyama, T., et al., *Nucleic Acids Res.* 2010, 38, 4834-4843; Yang, C.-G., et al., *Nature* 2008, 452, 961-965; Sundheim, O., et al., *EMBO J.* 2006, 25, 3389-3397; and Zhang, Z., et al., *ACS Chem. Biol.* 2016, 11, 1729-1736, the disclosures of which are incorporated herein by reference.) As shown in FIG. 11, the activity of these enzymes remains relatively high in the presence of an OGG1 inhibitor in accordance with various embodiments, which indicates that inhibition by the inhibitors of some embodiments against these enzymes is relatively low. As such, inhibitors of various embodiments show selectivity for OGG1 over other repair enzymes.

In a specific embodiment, FIG. 11 illustrates the selectivity of compound 41 against MTH1, DUT, NUDT16, ABH2, ABH3, and SMUG1 at a concentration of 20 µM The activities to all enzymes of compound 41 were low, thus establishing high selectivity of compound 41 to OGG1.

Toxicity

Figure 12:
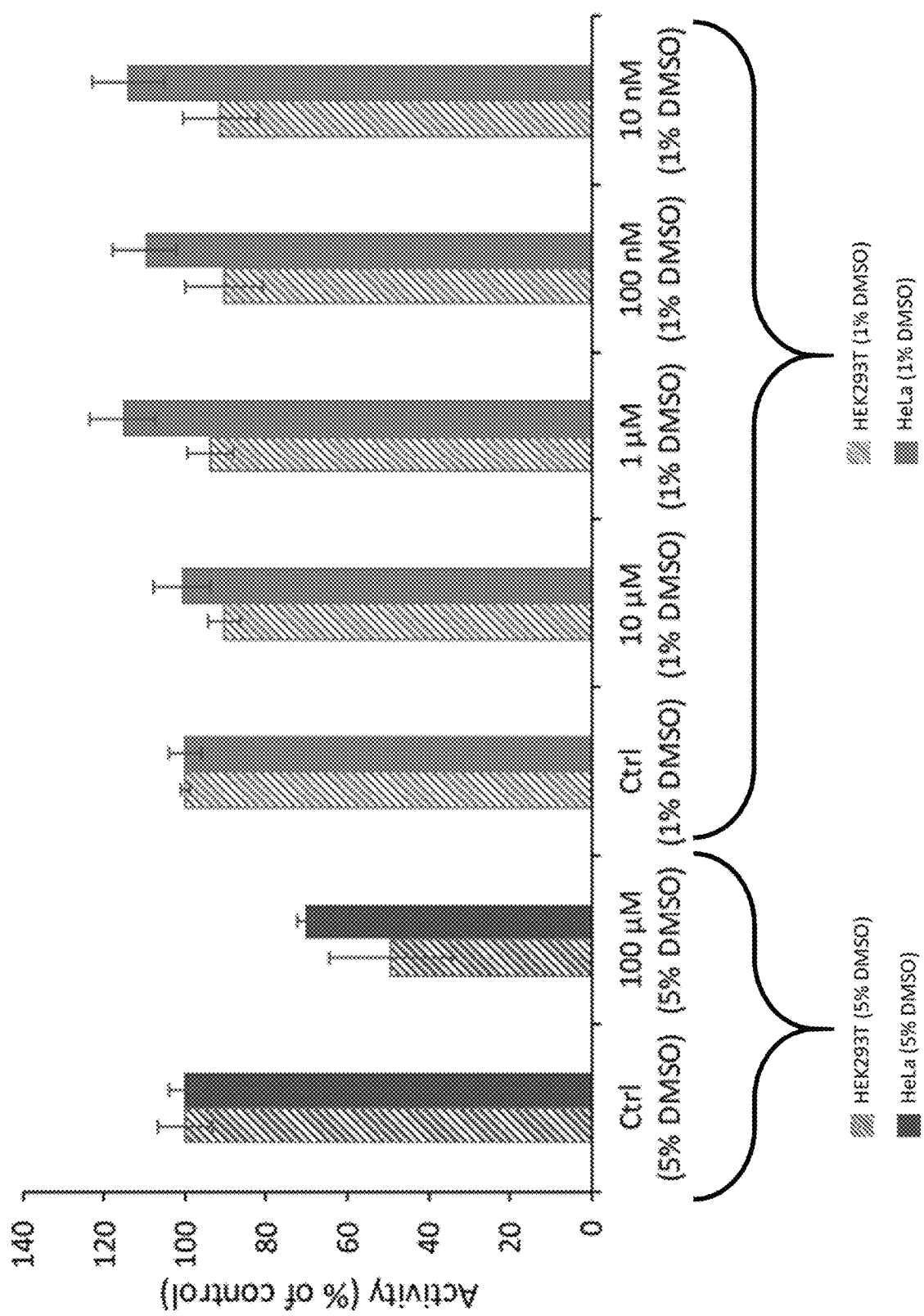
FIG. 12 provides a data plot of the toxicity of an exemplary OGG1 inhibitor by MTT assay with HEK293T and HeLa cell lines according to embodiments.

Additional embodiments will test the toxicity of certain inhibitors against cell lines. In some embodiments, the toxicity testing will use an MTT assay. FIG. 12 illustrates the toxicity of an inhibitor in accordance with various embodiments against two human cell lines (HEL293T and HeLa). In FIG. 12, the inhibitor shows little or no cytotoxicity in both cell lines at concentrations 10 nM to 10 µM, and exhibited moderate apparent toxicity only at the highest 100 µM concentration (30-50% toxicity). Thus, inhibitors in accordance with various embodiments are not toxic at concentrations above the $IC_{50}$.

As a specific embodiment, FIG. 12 illustrates the toxicity of compound 41 in two human cell lines (HEL293T and HeLa) by the MTT assay. Compound 41 showed little or no cytotoxicity in both cell lines at concentrations 10 nM to 10 µM, and exhibited moderate apparent toxicity only at the highest 100 µM concentration (30-50% toxicity). Thus, the compound is not significantly toxic at concentrations well above its $IC_{50}$.

Membrane Permeability

Additionally, certain embodiments possess membrane permeability properties. Table 9 summarizes membrane permeability in both the apical-to-basolateral and basolateral-to-apical directions. Recoveries based on the apical side (A-to-B) and basolateral side (B-to-A) were 65% and 79%, showing that various embodiments possess membrane permeability properties.

In the specific embodiment of compound 41, Table 9 summarizes the membrane permeability using the CACO-2 (clone C2BBel) assay, measuring permeability in both the apical-to-basolateral and basolateral-to-apical. Recoveries based on the apical side (A-to-B) and basolateral side (B-to-A) were 65% and 79%, showing that the permeability of compound 41 is satisfactory.

TABLE 9

CACO-2 assay with the OGG1 inhibitor 41

| | | $P_{app}$ ($10^{-6}$ cm/s) | | | |
|---|---|---|---|---|---|
| Direction | Recovery (%) | R1 | R2 | AVG | Efflux Ratio |
| A-to-B | 65 | 14.2 | 10.8 | 12.5 | |
| B-to-A | 79 | 63.5 | 91.3 | 77.4 | 6.2 |

Potency

Figure 13A:
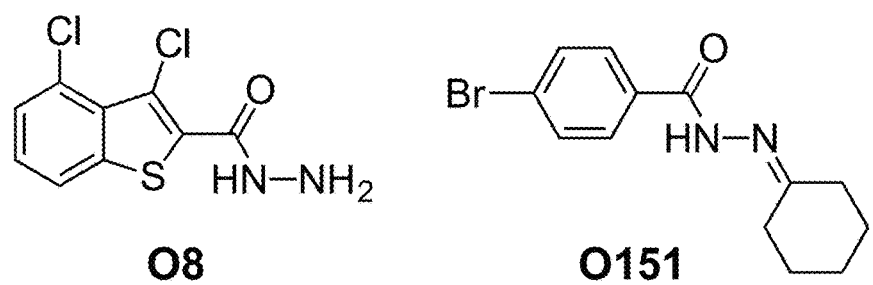
FIG. 13A provides diagrams of hydrazine and hydrazone inhibitors according to the prior art.
Figure 13B:
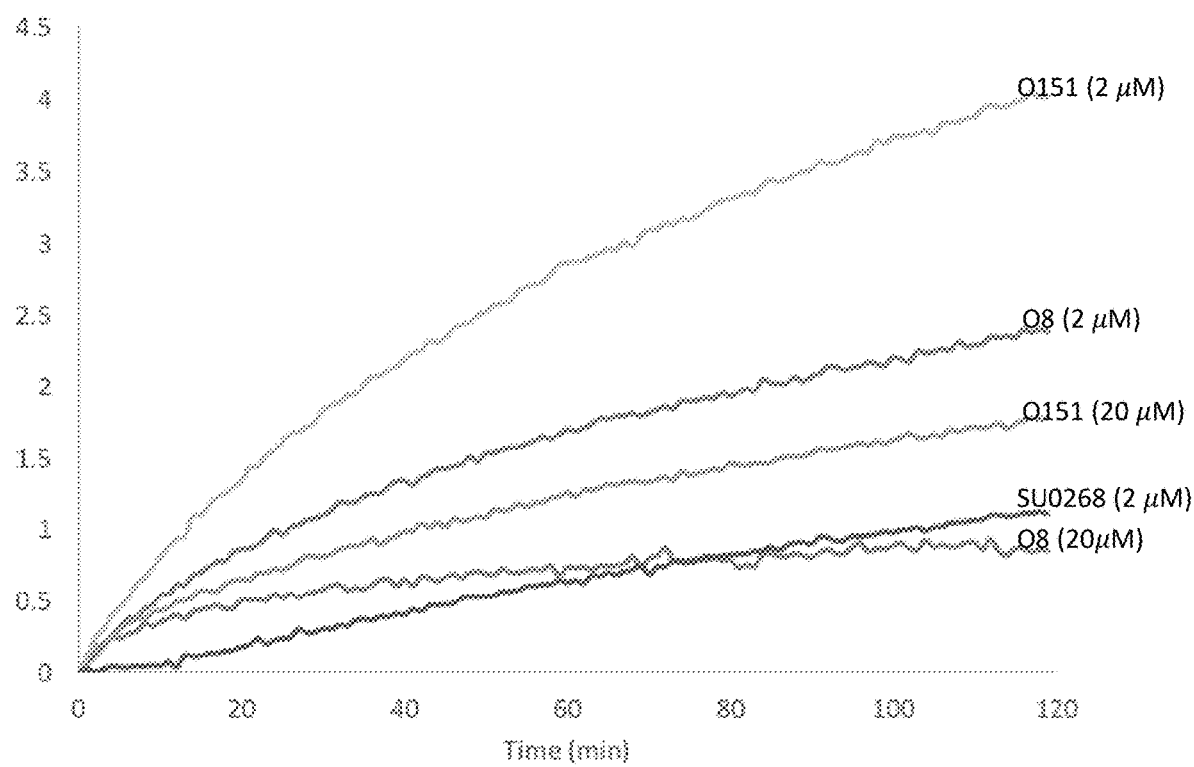
FIG. 13B provides a data plot of the activity of hydrazine and hydrazone inhibitors according to the prior art.

Certain embodiments of inhibitors in accordance with this disclosure are more potent than previously known OGG1 inhibitors. FIG. 13A illustrates a hydrazine inhibitor and a hydrazone inhibitor (O8 and O151) discovered in a previous report, which inhibit OGG1. (See, e.g., Donley, N., et al., *ACS Chem. Biol.* 2015, 10, 2334-2343, the disclosure of which is incorporated herein by reference.) FIG. 13B illustrates a comparison of these inhibitors against an inhibitor in accordance with embodiments of this disclosure (SU0268) using a base excision assay using the OGR1 probe. FIG. 13B demonstrates that inhibitors in accordance with certain embodiments are more potent than prior compounds (enzyme activity, % of control at were 45% at 20 µM, 69% at 2 µM (O8), and 62% at 20 µM, 100% at 2 µM (O151)). Of note, the prior compounds exhibit delayed kinetics of inhibition, which is consistent with the notion that the enzyme must first excise the 8-OG base before the compounds can be active. In contrast, the inhibitor SU0268 directly inhibits base excision, the first step of repair of this lesion by this enzyme In the specific embodiment illustrated in FIG. 13B, compound 41 ($IC_{50}$=0.059 μM) shows higher potency than the prior compounds (O8 and O151) (enzyme activity, % of control at were 45% at 20 μM, 69% at 2 μM (O8), and 62% at 20 μM, 100% at 2 μM (O151)) by the initial rates method. As measured by the OGR1 assay, the current inhibitor SU0268 directly inhibits base excision, the first step of repair of this lesion by this enzyme.

Stability

Some embodiments are directed to OGG1 inhibitors possess increased stability based on a measure of half-life within an individual. For example, FIGS. 14A-14C list various data across three replicates of mice, which were administered OGG1 inhibitors in accordance with certain embodiments. Table 10 summarizes the half-life data of these various embodiments. As such, various embodiments will have half-lives of less than one hour, approximately 1 hour, approximately 2 hours, approximately 3 hours, approximately 4 hours, approximately 5 hours, approximately 6 hours, or greater than 6 hours.

The specific embodiments described in FIGS. 14A-14C and Table 10 demonstrate the ability of these embodiments to possess the various half-lives. As shown, SU0267 possesses a relatively short half-life of less than an hour, while SU0268 and SU0333 possess half-lives of approximately 4 hours and approximately 5.2 hours, respectively. As such, various embodiments can be selected for short half-lives or long half-lives, where such determinations may be beneficial for the use as a treatment for an individual.

TABLE 10

Half-life measurements of inhibitors

| Inhibitor | R1 (hr) | R2 (hr) | R3 (hr) | Mean (hr) | SD |
|---|---|---|---|---|---|
| SU0267 | 0.768 | 0.536 | 0.842 | 0.715 | 0.160 |
| SU0268 | 4.84 | 3.62 | 3.60 | 4.02 | 0.709 |
| SU0333 | 6.03 | 4.45 | 5.22 | 5.24 | 0.790 |

Summary of Characteristics

In summary, certain embodiments of inhibitors have been developed based on acyl tetrahydroquinoline sulfonamide skeletons and demonstrate high potency and selectivity for OGG1. The structure-activity relationships of these embodiments were outlined by synthesizing a broad range of analogs. Additionally, these embodiments show good membrane permeability and no cytotoxicity in HEK293T and HeLa cells at active concentrations.

Applications of OGG1 Inhibitors

Further embodiments are directed to applications of various inhibitors in accordance with this disclosure in a number of varied cellular and animal models. Some embodiments are directed to OGG1 inhibitors targeted at, for example, the relief or treatment of cancers or inflammation implicated by the activity of enzyme OGG1. The methods may include identifying a subject having, developing, or at-risk of developing disorders implicated by OGG1 activity and administering a therapeutically effective amount of an OGG1 inhibitor containing formulation. In some embodiments, other active or inactive ingredients may be added to the OGG1 inhibitor formulation. Identification of the subjects that are at-risk of developing such disorders can be performed in a number of ways, including but not limited to, identification by relevant symptoms.

In some embodiments, OGG1 inhibitors may be administered in a therapeutically effective amount as part of a course of treatment. The administration of the OGG1 inhibitors may be orally, intraperitoneally, intravenously, subcutaneously, or any combination thereof. As used in this context, to "treat" means to ameliorate at least one symptom of an OGG1 enzyme dependent disorder. A therapeutically effective amount can be an amount sufficient to prevent the onset of symptoms related to such disorders or to decrease the severity of one or more symptoms. In some embodiments, a therapeutically effective amount inhibits or reduces the development of one or more such symptoms in a patient. In other embodiments, a therapeutically effective amount is an amount to reduce the intensity or duration of the disorder.

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the microbial culture assays, tissue culture assays and animal studies can be used in formulating a range of dosage for use in humans or other hosts. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. Such information can be used to more accurately determine useful doses in a host to receive antibiotics.

An "effective amount" is an amount sufficient to effect beneficial or desired results. For example, a therapeutically effective amount is one that achieves the desired therapeutic effect. This amount can be the same or different from a prophylactically effective amount, which is an amount necessary to prevent onset of menopause or menopause symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

In some embodiments, one could infer, based on the mode of administration, the vehicle of administration, the timing of administration, the type of menopause symptoms and/or the desired result, the appropriate titer, volume, or concentration to administer or inject. Likewise, in many embodiments, the appropriate dose for an affected patient may be calculated from a clinical trial or a study in mouse, macaque, human or any other suitable animal.

In such embodiments, it will be understood that any OGG1 inhibitor formulation as described in the application, either based on structural components or exemplified embodiments, including mixtures, could be used to treat disorders. Examples of OGG1 inhibitor formulations that could be used in some embodiments include, but are not limited to: OGG1 inhibitor without any additional active ingredients, a combination of OGG1 inhibitor with one or more other active ingredient, wherein the additional active ingredient or ingredients are intended to address one or more known disorder implicated by OGG1 activity, a combination of OGG1 inhibitor with other active ingredients as needed to address the disorder in a single formulation. Likewise, in other embodiments, it will be understood that any form vehicle or excipient in conjunction with OGG1 inhibitor could be used.

OGG1 inhibitor in accordance with structure described or exemplified by embodiment can be considered a candidate therapeutic. Candidate OGG1 inhibitor or analogues can be converted into a therapeutic for one or more disorders implicated by OGG1 activity such as, for example, cancer or inflammation. Furthermore, the therapeutics containing OGG1 inhibitor may then be appropriately conjoined with a vehicle or excipient. Possible excipients include fillers, disentegrants, lubricants, glidants, binders, buffers, and/or any other compound or composition that can increase or maintain the efficacy, stability, and/or activity of the active, OGG1 inhibitor. Additionally, some formulations can include special coatings to mask taste and/or control release of OGG1 inhibitors by allowing the release at the proper location in the body or at a predicted or calculated rate. Such coatings can include sugar, varnish, wax, and/or any other coating known to mask the taste, or the coatings can be resistant to stomach acids, susceptible to alkaline pH, and/or dissolved by particular enzymes in a particular area of the body, such as duodenum, jejunum, and/or colon. Further, therapeutics in accordance with some embodiments are stored in the appropriate formulation buffer capable of maintaining potency during shelf-life. Likewise, administration of the therapeutic can be performed in any suitable buffer for the procedure.

EXEMPLARY EMBODIMENTS

Experiments were conducted to demonstrate the capabilities of the assays and inhibitors in accordance with embodiments. These results and discussion are not meant to be limiting, but merely to provide examples of operative devices and their features.

Materials & Methods $^1$H NMR spectra were recorded on Varian Inova 300 (300 MHz) spectrometers. The chemical shifts were reported in parts per million (δ) relative to internal standard TMS (0 ppm) for CDCl$_3$. The peak patterns are indicated as follows: s, singlet; d, doublet; t, triplet; dt, m, multiplet; q, quartet. The coupling constants, J, are reported in Hertz (Hz). $^{13}$C NMR spectra were obtained by Varian Inova 300. CDCl$_3$ was used as a NMR solvent (ACROS ORGANICS). Low-resolution mass spectra were measured on an ESI (Electro Spray Ionization) by the ACQUITY UPLC (Waters). High-resolution mass spectra (HRMS) were measured on an ESI by micrOTOF-Q II (BRUKER). Ultraviolet spectra were measured on a Varian Cary 300. Fluorescence intensities were measured on Fluoroskan Ascent Microplate Fluorometer. OGR1 probe was synthesized by using an Applied Biosystems 394 DNA/RNA synthesizer. ClogP and tPSA were calculated by Chem Draw. Analytical TLC was performed on ready-to-use plates with silica gel 60 (Merck, F254), Flash column chromatography was performed over Fisher Scientific silica gel (grade 60, 230-400 mesh). All reagents were weighed and handled in air and backfilled under argon at room temperature. Unless otherwise noted, all reactions were performed under an argon atmosphere. All chemicals were purchased from, ACROS ORGANICS, Alfa Aesar, Ark Pharm, Asta Tech, Combi-Blocks, Enamine, Matrix Scientific, Sigma-Aldrich and TCI and used without further purification.

Example 1: General Procedure for OGG1 Inhibitor Assay

Background: OGG1 is used in base excision repair (BER) of DNA; specifically, OGG1 excises 8-OG from DNA. An assay to measure the activity of OGG1 allows for the ability to measure the inhibitory properties of inhibitors in accordance with various embodiments.

Methods: Synthesized compounds and hOGG1 (100 nM) were incubated in NEBuffer 4 (1×) with BSA (1×) at 37° C. (15 min) in 100 µL reaction volumes in a black 96-well plate. (See, e.g., Edwards, S. K., et al., *ChemBioChem* 2015, 16, 1637-1646, the disclosure of which is incorporated herein by reference.) After that, OGR1 (1.2 µM) was added to the reaction mixture. Fluorescence at 460 nm was measured on a Thermo Fluoroskan Ascent FL fluorescence plate reader ($\lambda_{ex}$=355 nm). The slope of initial rate (12 min) was calculated, and % of control was used for inhibition activity. BSA, hOGG1 and NEBuffer 4 were purchased from New England Biolabs and used. UltraPure Distilled Water (Invitrogen) was purchased and used for the assay.

Conclusion: In this embodiment, the inhibition of OGG1 by various inhibitors in accordance with certain embodiments of inhibitors can be measured.

Example 2: Procedure for MTH1 Assay

Background: MTH1 is a DNA repair enzyme with similar properties of OGG1. An experiment to measure the effect of inhibitors in accordance with certain embodiments against MTH1 demonstrates the specificity for OGG1 of inhibitors in accordance with certain embodiments.

Methods: Compound 41 and MTH1 (500 nM) were incubated in 21.8 µL reaction volume PNK buffer (1×) solution of ARGO probe (ATP-linked chimeric nucleotide) (40 µM) at 30° C. (30 min). After that, 5 µL of this reaction solution was mixed with 20 µL of Kinase-Glo. Immediately, luminescence was measured on a Thermo Fluoroskan Ascent FL fluorescence plate reader. (See, e.g., Ji, D., et al., *J. Am. Chem. Soc.* 2016, 138, 9005-9008, the disclosure of which is incorporated herein by reference.) The slope of initial rate (6 min) was calculated, and % of control was used for inhibition activity. MTH1 was purchased from Abcam, PNK buffer was purchased from New England Biolabs, and Kinase-Glo was purchased from Promega.

Results: As illustrated in FIG. 11, MTH1 possessed >80% enzyme activity in the presence of the inhibitor, indicating that the inhibitor has minimal inhibitory effect on MTH1.

Conclusion: Compound 41 shows low inhibitory effect on MTH1.

Example 3: Procedure for NUDT16 Assay

Background: NUDT16 is a DNA repair enzyme with similar properties of OGG1. An experiment to measure the effect of inhibitors in accordance with certain embodiments against NUDT16 demonstrates the specificity for OGG1 of inhibitors in accordance with certain embodiments.

Methods: The standard 20 µL reaction contained: 50 mM Tris-HCl, 50 mM $MgCl_2$, 1 mM DTT, pH 8.5, 100 µM DUAL nucleotide, 10 nM NUDT16 and compound 41. After 1 h incubation at 37° C., 5 µL of this reaction solution was added to 20 µL Kinase-Glo Luminescent Kinase Assay reaction solution (prepared as instructed for the ATP determination kit) in a 96 well plate. The bioluminescence signal was recorded at 1 min intervals over 10 min.

Results: As illustrated in FIG. 11, NUDT16 possessed ~70% enzyme activity in the presence of the inhibitor, indicating that the inhibitor has minimal inhibitory effect on NUDT16.

Conclusion: Compound 41 shows low inhibitory effect on NUDT16.

Example 4: Procedure for ABH2 Assay

Background: ABH2 is a DNA repair enzyme with similar properties of OGG1. An experiment to measure the effect of inhibitors in accordance with certain embodiments against ABH2 demonstrates the specificity for OGG1 of inhibitors in accordance with certain embodiments.

Methods: Using an unreported ABH2 probe, the activity of ABH2 was measured against compound 41. Enzyme (0.5 µM) was pre-incubated for 5 minutes with 20 µM inhibitor or vehicle or at 37° C. in 50 mM HEPES buffer (pH 8.0) containing 75 µM $Fe(NH_4)_2(SO_4)_2$, 1 mM α-ketoglutarate, 2 mM Sodium ascorbate, 50 µg/ml BSA and 0.4 mg/ml Catalase. The probe (1 µM) was added and fluorescent signal plotted over 10 minutes to calculate initial rate. Inhibitor rates were normalized against the vehicle control rate.

Results: As illustrated in FIG. 11, ABH2 possessed >90% enzyme activity in the presence of the inhibitor, indicating that the inhibitor has minimal inhibitory effect on ABH2.

Conclusion: Compound 41 shows low inhibitory effect on ABH2.

Example 5: Procedure for ABH3 Assay

Background: ABH3 is a DNA repair enzyme with similar properties of OGG1. An experiment to measure the effect of inhibitors in accordance with certain embodiments against ABH3 demonstrates the specificity for OGG1 of inhibitors in accordance with certain embodiments.

Methods: Using the previously reported MAQ probe, the activity of hABH3 was measured against compound 41. Enzyme (0.5 µM) was pre-incubated for 5 minutes with 20 µM inhibitor or vehicle or at 37° C. in 50 mM HEPES buffer (pH 8.0) containing 75 µM $Fe(NH_4)_2(SO_4)_2$, (See, e.g., Beharry, A. A., et al., *J. Am. Chem. Soc.* 2016, 138, 3647-3650, the disclosure of which is incorporated herein by reference.) 1 mM α-ketoglutarate, 2 mM Sodium ascorbate, 50 µg/ml BSA and 0.4 mg/ml Catalase. The MAQ probe (1 µM) was added and fluorescent signal plotted over 10 minutes to calculate initial rate. Inhibitor rates were normalized against the vehicle control rate.3

Results: As illustrated in FIG. 11, ABH3 possessed ~100% enzyme activity in the presence of the inhibitor, indicating that the inhibitor has minimal inhibitory effect on ABH3.

Conclusion: Compound 41 shows low inhibitory effect on ABH3.

Example 6: Procedure for SMUG1 Assay

Background: SMUG1 is a DNA repair enzyme with similar properties of OGG1. An experiment to measure the effect of inhibitors in accordance with certain embodiments against SMUG1 demonstrates the specificity for OGG1 of inhibitors in accordance with certain embodiments.

Methods: Using the previously reported SMUG 1 probe, the activity of SMUG1 was measured against compound 41. (See, e.g., Ono, T., et al., *Nucleic Acids Res.* 2013, 41, e127-e127, the disclosure of which is incorporated herein by reference.) Enzyme (500 U/mL) was pre-incubated for 5 minutes with 20 µM inhibitor or vehicle or at 37° C. in 50 mM Tris (pH 7.4), 1 mM DTT and 0.5 mM EDTA. Probe 2 (1 µM) was added and the fluorescent signal was plotted over 15 minutes to calculate initial rate. Inhibitor rates were normalized against the vehicle control rate.

Results: As illustrated in FIG. 11, SMUG1 possessed ~100% enzyme activity in the presence of the inhibitor, indicating that the inhibitor has minimal inhibitory effect on SMUG1.

Conclusion: Compound 41 shows low inhibitory effect on SMUG1

Example 7: Procedure for $K_m$ and $K_{cat}$ Study

Background: $K_m$ and $K_{cat}$ are measures of enzyme activity and can change in the presence of inhibitory molecules. A study was performed to measure these changes to determine the activity of some embodiments of OGG1 inhibitors to determine whether these inhibitors exhibit competitive, uncompetitive, or noncompetitive inhibition of OGG1.

Methods: For Michaelis-Menten curves: Inhibitor 41 and hOGG1 (100 nM) were incubated in NEBuffer 4 (1×) with BSA (1×) at 37° C. (15 min) in 100 µL reaction volumes in a black 96-well plate. After that, OGR1 (0.8-10 µM) was added to the reaction mixture. Fluorescence at 460 nm was measured on a Thermo Fluoroskan Ascent FL fluorescence plate reader (Aex=355 nm). The initial rate (12 min) was calculated. Lineweaver-Burk plot was leaded from the Michaelis-Menten curves. $K_m$ and $V_{max}$ were calculated from the equation. $K_{cat}$ was calculated from $K_{cat}=V_{max}/$[enzyme].

Figure 9:
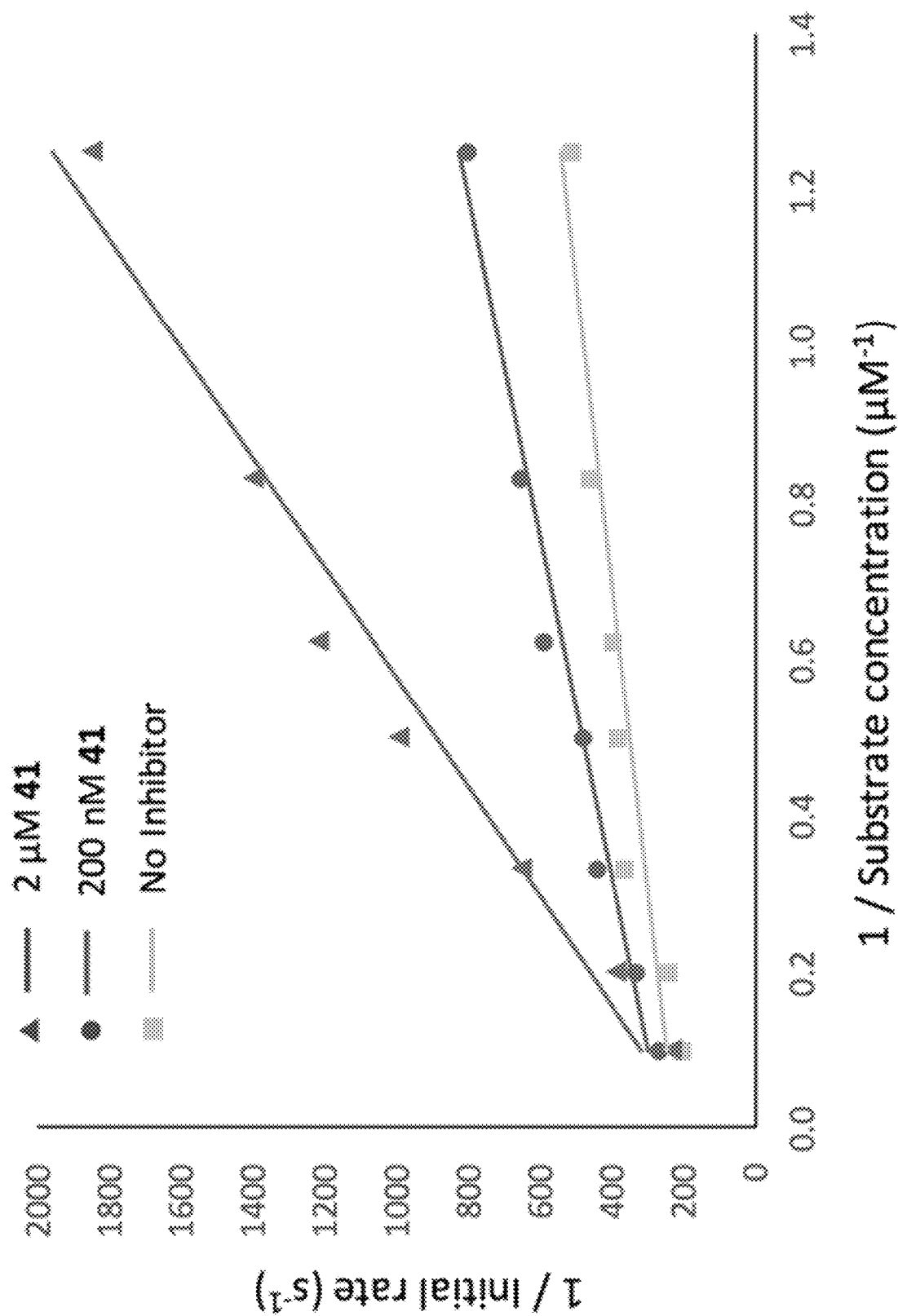
FIG. 9 provides a data plot of Lineweaver-Burk plots of OGG1 activity without inhibitor and with inhibitor according to embodiments.

Results: As illustrated in FIG. 9 and summarized in Table 7, the effect of the inhibitor on OGG1 had little to no effect on $K_m$ and a lowering of $K_{cat}$.

Conclusion: This study indicates that compound 41 is possibly a noncompetitive inhibitor against OGG1.

Example 8: Procedure for $T_m$ Study

Background: An interaction of a compound and DNA will change the melting temperature ($T_m$) of the DNA. A study was undertaken of abasic DNA and the OGR1 probe to measure the effect on $T_m$ caused by an inhibitor of an embodiment of this disclosure.

Methods: Abasic DNA: NEBuffer 4 (1×), 1 µM abasic DNA, 2 µM compound 41 (1% DMSO) were in 1600 µL reaction volumes with 1 cm path-length quartz cells. UV spectrum at 260 nm was measured on a Varian Cary 300. The $T_m$ value was calculated by Meltwin.

OGR1 probe: PBS buffer (0.1×), 1 µM OGR1 probe, 2 µM compound 41 (10% DMSO) were in 800 µL reaction volumes with 1 cm path-length quartz cells. UV spectrum at 260 nm was measured on a Varian Cary 300. The $T_m$ value was calculated by Meltwin.

Results: As summarized in Table 8, the $T_m$ of the DNA did not change significantly in the presence of compound 41.

Conclusion: Compound 41 does not interact with DNA, thus likely interacts directly with OGG1.

Example 9: Procedure for MTT Assay

Background: An MTT assay is a colorimetric assay for assessing cell metabolic activity. A reduction in metabolic activity is an indicator of toxicity to the cell. A study was undertaken to measure this effect as a measure of toxicity of a compound in accordance with some embodiments against two human cell lines.

Methods: HEK293T cells (concentration of 1.6×10^4 cells per well) and HeLa cells (concentration of 1.2×10^4 cells per well) were seeded to 96-well plate in supplemented DMEM culture medium (10% FBS, 100 U Pen./Strep.) and incubated for 30 h (HEK293T cells) and 16 h (HeLa cells) at +37° C. and 5% $CO_2$. These were incubated in 100 µL at a concentration of 100 µM, 10 µM, 1 µM, 100 nM, and 10 nM compound 41 for 24 h at +37° C. and 5%, in supplemented DMEM culture medium. After the incubation period, 10 µL of the MTT labeling reagent (final concentration 0.5 mg/ml) was added to each well, and incubated at +37° C. and 5%. 100 µl of the solubilization solution was added into each well, and incubated for 20 h at +37° C. and 5%. Absorbance of the samples was measured by using a microplate reader Tecan Infinite M1000 at 550, and 650 nm. Compound 41 was provided in concentration of 2 mM in DMSO that determined final concentration of DMSO in 100 µM at the level of 5%. In the rest of the samples (10 µM, 1 µM, 100 nM, and 10 nM) concentration of DMSO was at the level of 1%. The controls were prepared: Ctrl—cells cultured only in the supplemented DMEM; Ctrl 5% DMSO—cells cultured in 5% DMSO in the supplemented DMEM; Ctrl 1% DMSO—cells cultured in 1% DMSO in the supplemented DMEM.

Results: As summarized in FIG. 12, cellular activity maintained near 100% between 10 nM AND 10 µM of compound 41. At 100 µM of compound 41, cellular activity reduced ~30-50%

Conclusion: Compound 41 possess low levels of toxicity through the $IC_{50}$ dose of this compound.

Example 10: Procedure for CACO-2 Assay

Background: Membrane permeability may be important for an OGG1 inhibitor to reach the site of OGG1 activity in the nucleus and/or mitochondria. As such, a study to measure membrane permeability was undertaken.

Methods: Caco-2 cells (clone C2BBe1) were obtained from American Type Culture Collection (Manassas, Va.). Cell monolayers were grown to confluence on collagen-coated, microporous membranes in 12-well assay plates. Details of the plates and their certification are shown below. The permeability assay buffer was Hanks' balanced salt solution containing 10 mM HEPES and 15 mM glucose at a pH of 7.4. The buffer in the receiver chamber also contained 1% bovine serum albumin. The dosing solution concentration was 5 µM of test article in the assay buffer. Cell monolayers were dosed on the apical side (A-to-B) or basolateral side (B-to-A) and incubated at 37° C. with 5% $CO_2$ in a humidified incubator. Samples were taken from the donor and receiver chambers at 120 minutes. Each determination was performed in duplicate. The flux of Lucifer yellow was also measured post-experimentally for each monolayer to ensure no damage was inflicted to the cell monolayers during the flux period. All samples were assayed by LC-MS/MS using electrospray ionization.

Results: As summarized in Table 9, 65-79% of compound 41 was recovered after passing through the membrane.

Conclusion: Compound 41 possess satisfactory levels of membrane permeability.

Example 11: Procedure for Determining Half-Life

Background: Pharmaceutical half-life is a measure of stability of a compound in an individual. Longer half-lives indicate a slower clearance rate for the particular compound, thus allowing an increased concentration of the compound to circulate within a body. To measure the stability of various embodiments, a study was undertaken to determine the half-lives of these embodiments.

Methods: Each OGG1 inhibitor was dosed by intraperitoneal (IP) and oral (PO) routes of administration at a target dose of 3 mg/kg. Blood samples were collected up to 24 hours post-dose, and blood concentrations of the test articles were determined by LC-MS/MS. Pharmacokinetic parameters were determined using Phoenix WinNonlin (v8.0) software Results: As shown in FIG. 14A, following IP dosing of SU0267, maximum blood concentrations (average of 425±14.7 ng/mL) were observed between 5 and 30 minutes hour post dosing. The average half-life after intraperitoneal dosing was 0.715±0.160 hours. The average exposure for SU0267 based on the dose-normalized $AUC_{last}$ was 134±4.09 hr*kg*ng/m g.

As shown in FIG. 14B, following IP dosing of SU0268, maximum blood concentrations (average of 1210±206 ng/mL) were observed at 15 minutes hour post dosing. The average half-life after intraperitoneal dosing was 4.02±0.709 hours. The average exposure for SU0268 based on the dose-normalized $AUC_{last}$ was 543±281 hr*kg*ng/m L/m g.

As shown in FIG. 14C, following IP dosing of SU0333, maximum blood concentrations (average of 714±343 ng/mL) were observed at 15 minutes hour post dosing. The average half-life after intraperitoneal dosing was 5.24±0.790 hours. The average exposure for SU0333 based on the dose-normalized $AUC_{last}$ was 454±209 hr*kg*ng/m L/m g.

Conclusion: Various embodiments can reach peak levels of blood concentration within 30 minutes and can be selected for and/or augmented to adjust half-life length and stability.

DOCTRINE OF EQUIVALENTS

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A compound of formula ABCDE:

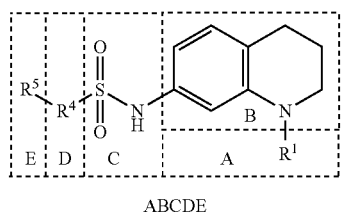

ABCDE wherein:
A is $R^1$;
B is 1,2,3,4-tetrahydroquinolin-1,7-diyl;
C is —NHS(O)$_2$—;
D is —$R^4$—;
E is $R^5$;
$R^1$ is C(O)$R^{10}$;
$R^4$ is phenylene;
  wherein the phenylene is optionally substituted with 1 or more substituents independently selected from the group consisting of D, halogen, B(OR)$_2$, CN, alkyl, haloalkyl, C(O)R, C(O)N(R)$_2$, C(O)OR, NC, NCO, NCS, N$_3$, NO$_2$, N(R)$_2$, NRC(O)R, NRC(O)N(R)$_2$, NRC(O)OR, NRS(O)$_2$R, NRS(O)$_2$N(R)$_2$, OCN, OC(O)R, OC(O)N(R)$_2$, ONO$_2$, OP(O)(OR)$_2$, OR, SCN, SR, S(O)R, S(O)$_2$R, S(O)$_2$N(R)$_2$, S(O)$_2$OR, cycloalkyl, heterocycloalkyl, aryl, and heteroaryl;
$R^5$ is phenyl;
  wherein the phenyl is optionally substituted with 1 or more substituents independently selected from the group consisting of D, halogen, B(OR)$_2$, CN, alkyl, alkenyl, alkynyl, C(O)R, C(O)N(R)$_2$, C(O)OR, NC, NCO, NCS, N$_3$, NO$_2$, N(R)$_2$, NRC(O)R, NRC(O)N(R)$_2$, NRC(O)OR, NRS(O)$_2$R, NRS(O)$_2$N(R)$_2$, OCN, OC(O)R, OC(O)N(R)$_2$, ONO$_2$, OP(O)(OR)$_2$, OR, SCN, SR, S(O)R, S(O)$_2$R, S(O)$_2$N(R)$_2$, S(O)$_2$OR, cycloalkyl, heterocycloalkyl, aryl, and heteroaryl;
$R^{10}$ is $C_{1-4}$ alkyl, $C_{1-4}$ alkylene-aryl, cyclopropyl, or cyclobutyl;
  wherein the $C_{1-4}$ alkyl of $R^{10}$ is optionally substituted with 1 or more substituents independently selected from the group consisting of D, halogen, B(OR)$_2$, CN, NCS, N$_3$, NO$_2$, N(R)$_2$, ONO$_2$, OP(O)(OR)$_2$, OR, SCN, SR, S(O)$_2$R, and S(O)$_2$OR;
  wherein the aryl of the $C_{1-4}$ alkylene-aryl is optionally substituted with 1 or more substituents independently selected from the group consisting of D, halogen, B(OR)$_2$, CN, alkyl, NCS, N$_3$, NO$_2$, N(R)$_2$, ONO$_2$, OP(O)(OR)$_2$, OR, SCN, SR, S(O)$_2$R, and S(O)$_2$OR;
  wherein the cyclopropyl of $R^{10}$ is optionally substituted with 1 CH$_3$ substituent and/or optionally further substituted with 1 or more additional substituents independently selected from the group consisting of D, halogen, B(OR)$_2$, CN, NCS, N$_3$, NO$_2$, N(R)$_2$, ONO$_2$, OP(O)(OR)$_2$, OR, SCN, SR, S(O)$_2$R, and S(O)$_2$OR;
  wherein the CH$_3$ substituent of the cyclopropyl of $R^{10}$ is optionally substituted with 1 or more substituents independently selected from the group consisting of D and halogen; and
  wherein the cyclobutyl of $R^{10}$ is optionally substituted with 1 or more substituents independently selected from the group consisting of D, halogen, B(OR)$_2$, CN, NCS, N$_3$, NO$_2$, N(R)$_2$, ONO$_2$, OP(O)(OR)$_2$, OR, SCN, SR, S(O)$_2$R, and S(O)$_2$OR; and
each R is independently H, D, $C_{1-4}$ alkyl, $C_{2-4}$ alkenyl, $C_{2-4}$ alkynyl, cyclopropyl, or cyclobutyl, wherein each $C_{1-4}$ alkyl, $C_{2-4}$ alkenyl, $C_{2-4}$ alkynyl, cyclopropyl, and cyclobutyl is optionally and independently substituted with 1 or more substituents independently selected from the group consisting of D, halogen, B(OH)$_2$, B(OC$_{1-4}$ alkyl)$_2$, CN, NCS, N$_3$, NO$_2$, NH$_2$, NHC$_{1-4}$alkyl, N(C$_{1-4}$alkyl)$_2$, ONO$_2$, OP(O)(OH)$_2$, OP(O)(OC$_{1-4}$ alkyl)$_2$, OH, OC$_{1-4}$ alkyl, SCN, SH, SC$_{1-4}$ alkyl, S(O)$_2$H, S(O)$_2$C$_{1-4}$ alkyl, S(O)$_2$OH, S(O)$_2$OC$_{1-4}$ alkyl, cycloalkyl, heterocycloalkyl, aryl, and heteroaryl; or
  each R, taken together with the atom(s) to which they are attached, optionally and independently forms a ring.

2. The compound of claim 1, wherein $R^4$ is phenylene, wherein the phenylene is optionally substituted with 1 or more substituents independently selected from the group consisting of halogen, B(OR)$_2$, CN, alkyl, haloalkyl, C(O)R, C(O)N(R)$_2$, C(O)OR, NC, NCO, NCS, N$_3$, NO$_2$, N(R)$_2$, NRC(O)R, NRC(O)N(R)$_2$, NRC(O)OR, NRS(O)$_2$R, NRS(O)$_2$N(R)$_2$, OCN, OC(O)R, OC(O)N(R)$_2$, ONO$_2$, OP(O)(OR)$_2$, OR, SCN, SR, S(O)R, S(O)$_2$R, S(O)$_2$N(R)$_2$, S(O)$_2$OR, cycloalkyl, heterocycloalkyl, aryl, and heteroaryl.

3. The compound of claim 1, wherein $R^4$ is phenylene, wherein the phenylene is optionally substituted with 1 substituent selected from the group consisting of halogen, cyclohexyl, phenyl, pyrazolyl, and pyridyl.

4. The compound of claim 1, wherein $R^{10}$ is CH$_3$, CH$_2$CH$_3$, cyclopropyl, or cyclobutyl;
  wherein the CH$_3$ or CH$_2$CH$_3$ is optionally substituted with 1 or more substituents independently selected from the group consisting of D, halogen, B(OR)$_2$, CN, NCS, N$_3$, NO$_2$, N(R)$_2$, ONO$_2$, OP(O)(OR)$_2$, OR, SCN, SR, S(O)$_2$R, and S(O)$_2$OR;
  wherein the cyclopropyl is optionally substituted with 1 CH$_3$ substituent and/or optionally further substituted with 1 or more additional substituents independently selected from the group consisting of D, halogen, B(OR)$_2$, CN, NCS, N$_3$, NO$_2$, N(R)$_2$, ONO$_2$, OP(O)(OR)$_2$, OR, SCN, SR, S(O)$_2$R, and S(O)$_2$OR; and
  wherein the CH$_3$ substituent of the cyclopropyl is optionally substituted with 1 or more substituents independently selected from the group consisting of D and halogen.

5. The compound of claim 1, wherein $R^5$ is phenyl, wherein the phenyl is optionally substituted with 1 substituent selected from the group consisting of C(O)NH$_2$, N(CH$_3$)$_2$, NHC(O)CH$_3$, OCH$_3$, cyclohexyl, phenyl, pyrazolyl, and pyridyl.

6. The compound of claim 1, wherein:

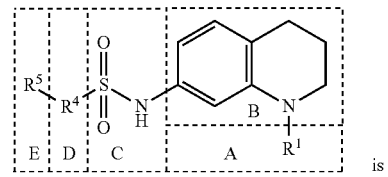

is

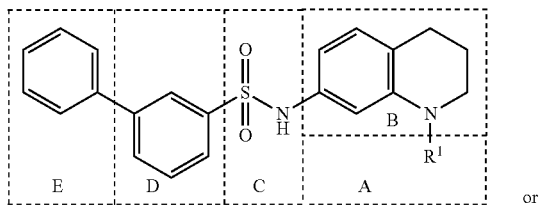

or

-continued

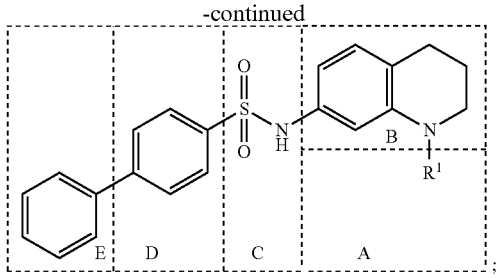

D is optionally substituted with 1 or more substituents independently selected from the group consisting of D, halogen, $B(OR)_2$, CN, alkyl, haloalkyl, C(O)R, C(O)N(R)$_2$, C(O)OR, NC, NCO, NCS, N$_3$, NO$_2$, N(R)$_2$, NRC(O)R, NRC(O)N(R)$_2$, NRC(O)OR, NRS(O)$_2$R, NRS(O)$_2$N(R)$_2$, OCN, OC(O)R, OC(O)N(R)$_2$, ONO$_2$, OP(O)(OR)$_2$, OR, SCN, SR, S(O)R, S(O)$_2$R, S(O)$_2$N(R)$_2$, S(O)$_2$OR, cycloalkyl, heterocycloalkyl, aryl, and heteroaryl;

E is optionally substituted with 1 substituent selected from the group consisting of D, halogen, $B(OR)_2$, CN, alkyl, alkenyl, alkynyl, C(O)R, C(O)N(R)$_2$, C(O)OR, NC, NCO, NCS, N$_3$, NO$_2$, N(R)$_2$, NRC(O)R, NRC(O)N(R)$_2$, NRC(O)OR, NRS(O)$_2$R, NRS(O)$_2$N(R)$_2$, OCN, OC(O)R, OC(O)N(R)$_2$, ONO$_2$, OP(O)(OR)$_2$, OR, SCN, SR, S(O)R, S(O)$_2$R, S(O)$_2$N(R)$_2$, S(O)$_2$OR, cycloalkyl, heterocycloalkyl, aryl, and heteroaryl; and $R^{10}$ is $C_{1-4}$ alkyl or cyclopropyl.

7. A pharmaceutical formulation comprising a pharmaceutically acceptable excipient and a compound of claim 1.

8. The pharmaceutical formulation of claim 7, wherein the pharmaceutically acceptable excipient is selected from the group consisting of a binder, a buffer, a disintegrant, a filler, a glidant, and a lubricant.

9. A method for inhibiting repair enzyme 8-oxoguanine deoxyribonucleic acid glycosylase activity in an individual, wherein the method comprises administering to the individual in need thereof a therapeutically effective amount of the compound of claim 1.

10. The method of claim 9, wherein the administering step is performed by intraperitoneal injection.

11. A method for inhibiting repair enzyme 8-oxoguanine deoxyribonucleic acid glycosylase activity in an individual, wherein the method comprises administering to the individual in need thereof a therapeutically effective amount of the pharmaceutical formulation of claim 7.

12. The method of claim 11, wherein the pharmaceutically acceptable excipient is selected from the group consisting of a binder, a buffer, a disintegrant, a filler, a glidant, and a lubricant.

* * * * *